(12) United States Patent
Shelton, IV et al.

(10) Patent No.: US 11,071,619 B2
(45) Date of Patent: Jul. 27, 2021

(54) COUPLING ASSEMBLY FOR IMPLANTABLE SPHINCTER ASSISTANCE DEVICE

(71) Applicant: Ethicon LLC, Guaynabo, PR (US)

(72) Inventors: Frederick E. Shelton, IV, Hillsboro, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 164 days.

(21) Appl. No.: 16/221,813

(22) Filed: Dec. 17, 2018

(65) Prior Publication Data

US 2020/0188081 A1     Jun. 18, 2020

(51) Int. Cl.
| | |
|---|---|
| *A61F 2/04* | (2013.01) |
| *A61B 17/12* | (2006.01) |
| *A61B 17/00* | (2006.01) |
| *A61B 18/00* | (2006.01) |

(52) U.S. Cl.
CPC .......... *A61F 2/04* (2013.01); *A61B 17/12099* (2013.01); *A61B 2017/00818* (2013.01); *A61B 2018/00553* (2013.01); *A61F 2002/044* (2013.01); *A61F 2210/009* (2013.01)

(58) Field of Classification Search
CPC ...... A61F 2/04; A61F 2002/044; A61F 5/005; A61F 5/0065; A61F 5/0066; A61F 5/0073
See application file for complete search history.

(56) References Cited

U.S. PATENT DOCUMENTS

| | | | |
|---|---|---|---|
| 5,122,136 A | 6/1992 | Guglielmi et al. | |
| 5,204,382 A | 4/1993 | Wallace et al. | |
| 5,509,888 A | 4/1996 | Miller | |
| 5,702,361 A | 12/1997 | Evans, II et al. | |
| 6,543,456 B1 | 4/2003 | Freeman | |
| 7,175,589 B2 | 2/2007 | Deem et al. | |

(Continued)

FOREIGN PATENT DOCUMENTS

| | | |
|---|---|---|
| DE | 3011742 A1 | 10/1981 |
| EP | 1547549 A2 | 6/2005 |

(Continued)

OTHER PUBLICATIONS

U.S. Appl. No. 15/908,875, entitled Laparoscopic Sizing Instrument, filed Mar. 3, 2018.

(Continued)

*Primary Examiner* — Carrie R Dorna
(74) *Attorney, Agent, or Firm* — Frost Brown Todd LLC

(57) ABSTRACT

An artificial sphincter and method closing the artificial sphincter includes a plurality of bodies, a plurality of links, a coupling body, and a coupling assembly. The plurality of bodies each have respective magnets and are arranged from a first terminal body to a second terminal body. The plurality of links respectively resiliently extend and connect between the plurality of bodies. The coupling body has a first end segment and a second end segment respectively connected to a first terminal link and a second terminal link respectively extending from the first and second end segments. The coupling assembly has a clasp configured to close to form a closed loop and a coupling guide configured to be manipulated to thereby orient portions of the clasp to a predetermined orientation for connection in the connected state.

20 Claims, 12 Drawing Sheets

(56) References Cited

U.S. PATENT DOCUMENTS

| | | | |
|---|---|---|---|
| 7,374,565 B2 | 5/2008 | Hassler, Jr. et al. | |
| 7,390,294 B2 | 6/2008 | Hassler, Jr. | |
| 7,445,010 B2 | 11/2008 | Kugler et al. | |
| 7,481,763 B2 | 1/2009 | Hassler, Jr. et al. | |
| 7,695,427 B2 | 4/2010 | Kugler et al. | |
| 7,727,141 B2 | 6/2010 | Hassler, Jr. et al. | |
| 7,879,068 B2 | 2/2011 | Dlugos et al. | |
| 8,070,670 B2 | 12/2011 | Deem et al. | |
| 8,603,023 B2 | 12/2013 | Albrecht et al. | |
| 8,617,049 B2 | 12/2013 | Dlugos, Jr. et al. | |
| 8,636,751 B2 | 1/2014 | Albrecht et al. | |
| 8,715,157 B2 | 5/2014 | Berg et al. | |
| 8,734,475 B2 | 5/2014 | Ekvall et al. | |
| 8,870,742 B2 | 10/2014 | Dlugos, Jr. et al. | |
| 8,876,761 B2 | 11/2014 | Albrecht et al. | |
| 10,405,865 B2 | 9/2019 | Shelton, IV et al. | |
| 2004/0230137 A1* | 11/2004 | Mouton | A61F 5/0083 600/593 |
| 2005/0002984 A1* | 1/2005 | Byrum | A61F 5/0056 424/423 |
| 2005/0283235 A1 | 12/2005 | Kugler et al. | |
| 2008/0146869 A1* | 6/2008 | Chow | A61F 5/005 600/37 |
| 2009/0062824 A1 | 3/2009 | Berg et al. | |
| 2011/0098731 A1 | 4/2011 | Whitbrook et al. | |
| 2012/0041458 A1* | 2/2012 | Paganon | A61F 2/004 606/151 |
| 2014/0336696 A1 | 11/2014 | Kugler et al. | |
| 2017/0055986 A1 | 3/2017 | Harris et al. | |
| 2019/0029689 A1 | 1/2019 | Shelton, IV et al. | |

FOREIGN PATENT DOCUMENTS

| | | |
|---|---|---|
| WO | WO 1993/015721 A1 | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |
| WO | WO 2013/165541 A1 | 11/2013 |
| WO | WO 2018/001192 A1 | 1/2018 |

OTHER PUBLICATIONS

U.S. Appl. No. 15/914,381, entitled "Tunable Magnetic Sphincter Augmentation Device," filed Mar. 7, 2018.

U.S. Appl. No. 15/914,407, entitled "MRI Compatible Magnetic Sphincter Augmentation Device," filed Mar. 7, 2018.

International Search Report and Written Opinion dated Jun. 23, 2020 for Application No. PCT/IB2019/060727, 16 pgs.

\* cited by examiner

COUPLING ASSEMBLY FOR IMPLANTABLE SPHINCTER ASSISTANCE DEVICE

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which effects the esophagus.

A normal, heathy, esophagus is a muscular tube that carries food from the mouth, through the chest cavity and into the upper part of the stomach. A small-valved opening in the esophagus, called the lower esophageal sphincter ("LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
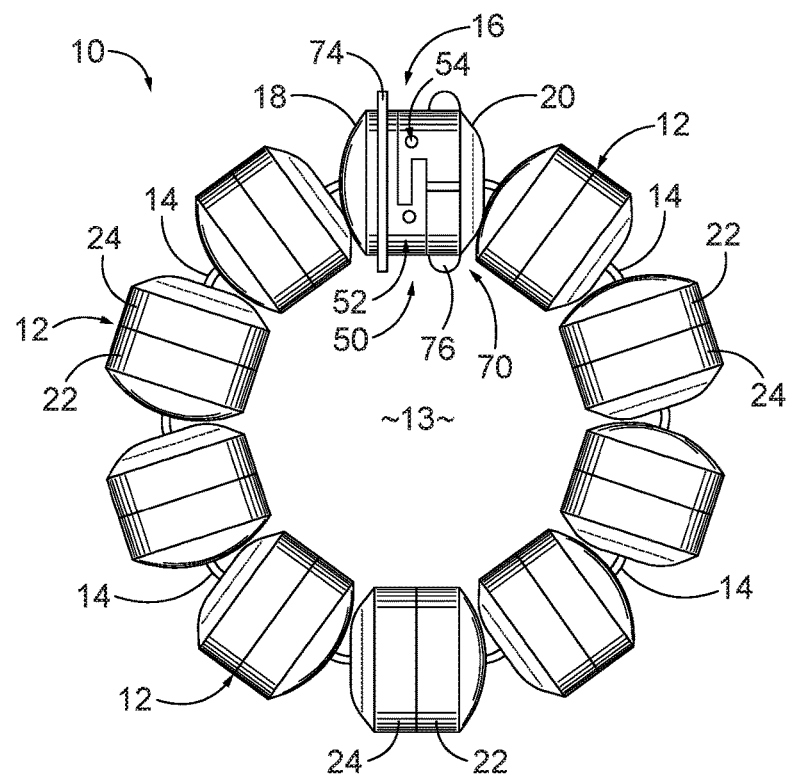
FIG. 1 depicts a top view of an exemplary artificial sphincter in a connected state with a closed loop for a gastrointestinal tract.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, to the extent that spatial terms such as "upper," "lower," "left," "right," "longitudinal," "radial," "transverse," "inner," "outer," "inward," "outward," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the term "approximately" for any numerical values or ranges indicate a suitable dimensional tolerance that allows the part or collection of components to function for its intended purpose as described herein.

I. Overview of an Exemplary Artificial Sphincter

Figure 2:
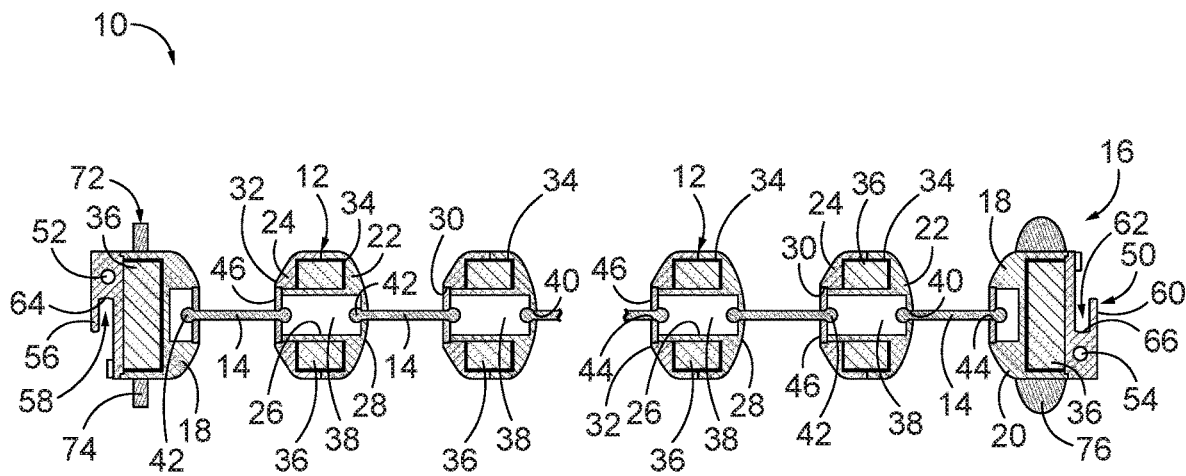
FIG. 2 depicts a sectional, top view of the artificial sphincter of FIG. 1 in a disconnected state.

FIG. 1 shows an exemplary artificial sphincter (10) includes a plurality of substantially cylindrical bodies (12), which are also referred to here as "beads" (12). Beads (12) can be formed into a closed loop with an open interior (13) as shown in FIG. 1. Beads (12) are strung together by a plurality of links (14) extending respectively between a pair of beads (12). Generally, each bead (12) of the present example has one link (14) extending therefrom to each of the immediately adjacent beads on each respective side of such bead (12). In contrast, a coupling bead (16) has a pair of left and right end segments (18, 20) respectively connected to left and right terminal end beads (20) by links (14). End segments (18, 20) removably connect together in a connected state to form the closed loop shown in FIG. 1, but disconnect in a disconnected state for initial separation from one another as shown in FIG. 2. This allows artificial sphincter (10) to, at least initially, be a flexible string of beads (12, 16) in an open state, which non-loop condition may be helpful in initially implanting the artificial sphincter (10) in a patient. If and when desired, end segments (18, 20) of coupling bead (16) may be connected to one another as discussed below in greater detail.

Figure 3:
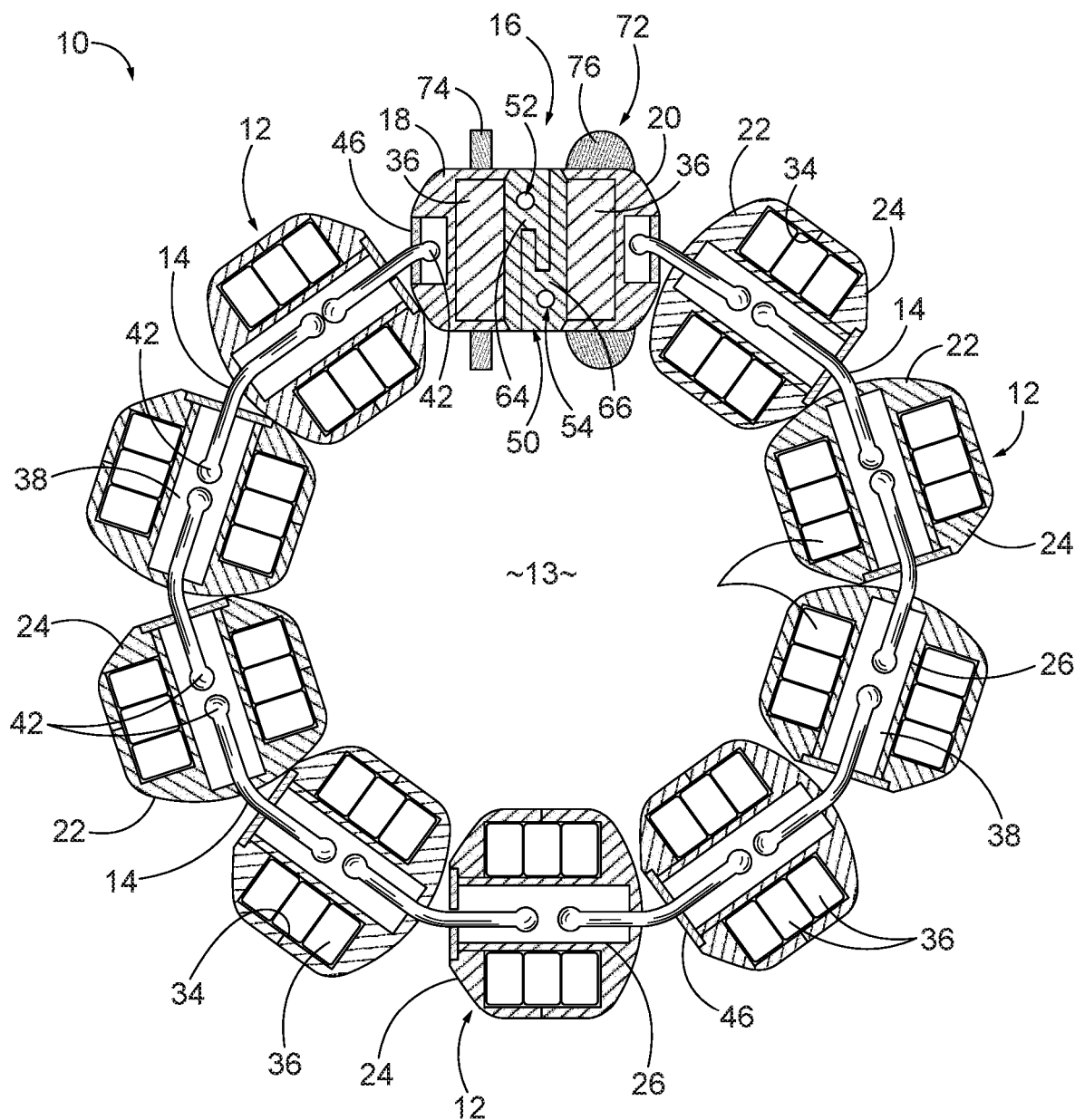
FIG. 3 depicts a sectional, top view of the artificial sphincter of FIG. 1 in a closed, contracted state.
Figure 4:
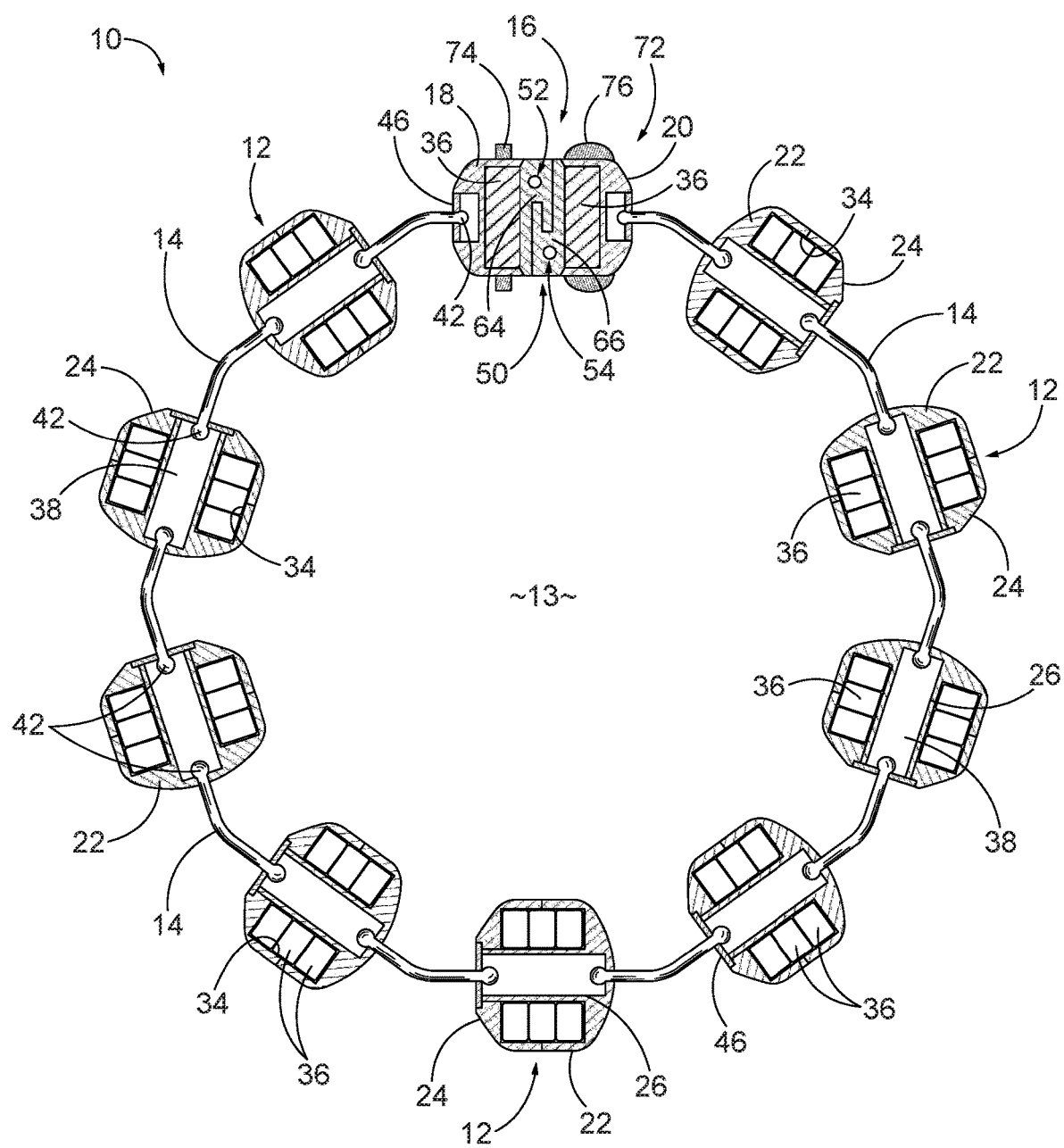
FIG. 4 depicts a sectional, top view of the artificial sphincter of FIG. 1 in a closed, expanded state.
Figure 5:
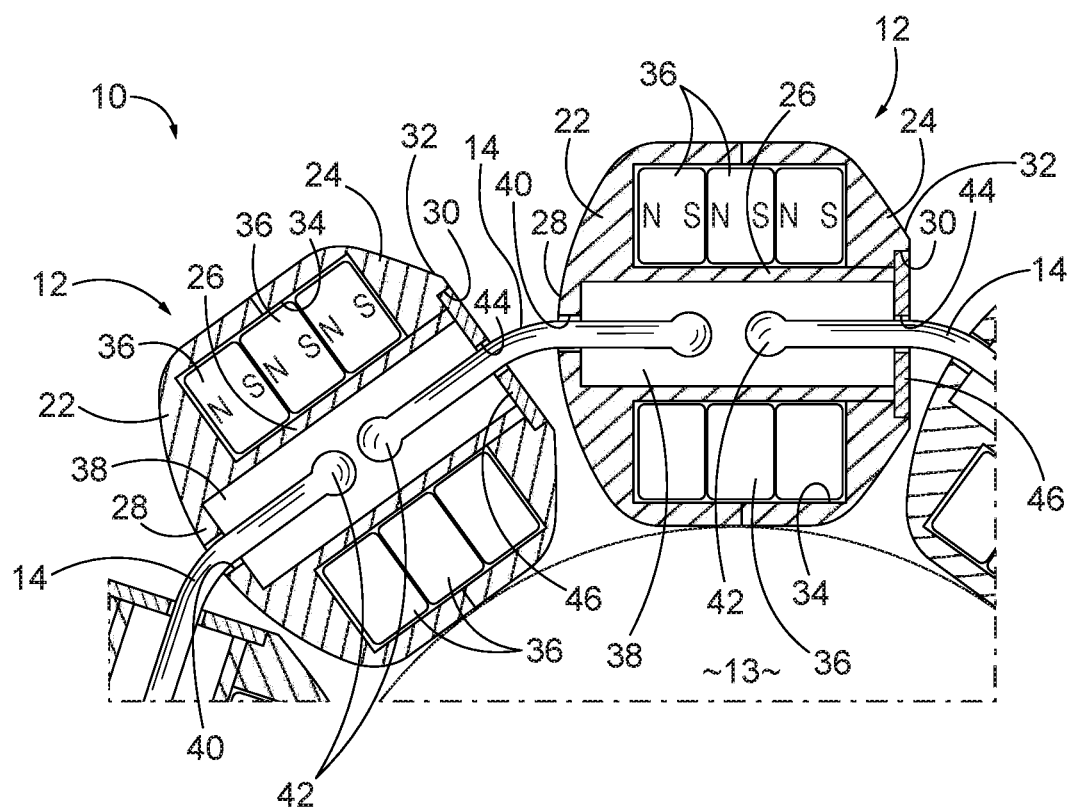
FIG. 5 depicts an enlarged, sectional view of the artificial sphincter of FIG. 1.

Each bead (12, 16) of artificial sphincter (10) resiliently attracts to adjacent beads (12, 16) in the string or loop. This resilient attraction may be provided by means such as magnetic force, spring force, or the like. FIGS. 3-5 show artificial sphincter (10) having magnetic force to attract adjacent beads (12, 16) to one another. To this end, each bead (12) includes two mating housing components (22, 24). Each housing component (22, 24) is generally cup-shaped. Each housing component (22) has a hollow post (26) standing up from a center of a bottom (28). The part of each post (26) that is most remote from a remainder of cup (22) extends into an aperture (30) in a bottom of the associated cup (24). End lips of cups (22, 24) annularly abut one another to form bead (12). Thus, the interiors of cups (22, 24) of bead (12) form a hollow annular space (34) inside bead (12) and concentrically around post (26) inside bead (12). One or more toroidal permanent magnets (36) are concentrically disposed about post (26) in hollow annular space (34). Magnets (36) are magnetically polarized so that magnets (36) in adjacent beads (12, 16) in the string or loop magnetically attract one another. Such polarity is indicated with an "N" for north polarization and an "S" for south polarization. This magnetic attraction resiliently attracts adjacent beads (12, 16) in the string or loop toward one another.

A hollow interior (38) of each post (26) is large enough to loosely accommodate end portions of two links (14). Within each bead (12), one of the associated links (14) extends out of an aperture (40) in bottom (28) of cup (22). Aperture (40) is large enough to allow the main length of link (14) to pass freely through aperture (40), but is small enough to inhibit an enlarged stop (42) at the end of link (14) to pass through aperture (40). The other link (14) associated with each bead (12) extends out of an aperture (44) in a center of a washer-like cap (46) that is used to substantially close aperture (30) in the bottom of cup (24) and the otherwise open end of hollow interior (38) in post (26). Again, aperture (44) in cap (46) is large enough to allow the main length of the associated link (14) to pass freely through, but is small enough to inhibit enlarged stop (42) at the end of link (14) to pass.

The various components of artificial sphincter (10) can be assembled, such as during manufacture, as follows. Each link (14) can be initially provided with one enlarged end stop (42). The other end of link (14) can be passed successively through aperture (40) in bottom (28) of cup (22), which is not yet attached to cup (24), and aperture (44) in cap (46), which is also not yet attached to cup (24). Another enlarged end stop (42) can be formed on the other end of link (14). Magnets (36) can be placed in cup (22). Cup (24) is then attached to cup (22) as well as cap (46).

Magnets (36) may or may not be biocompatible in the present example, because magnets (36) are completely sealed inside beads (12, 16). The parts of artificial sphincter (10) that will be exposed to patient are preferably biocompatible. These components include, but are not limited to, cups (22, 24) including posts (26), caps (46), and links (14). An example of a biocompatible material that is suitable for these components is titanium, but many other suitable metallic and non-metallic materials are known to those skilled in art and can be used if and as desired. Assuming that one or more metals are used for components (14, 22, 26, 24, 46), enlarged end stops (42) may be formed as weld balls, annular hermetic welds may be formed between abutting lips of cups (22, 24), a similar annular hermetic weld may be formed between mating components (26, 24), and spot welds may be used to secure caps (46) to associated cups (24). Hermetic sealing of this latter connection is not required because of the hermetic sealing between components (26, 24). Alternatively, the mating between components (26, 24) could be left unsealed, and a seal weld could be used between component (46) and components (26, 24). In the present example, the ends of each cylindrical bead (12) are preferably approximately spherical. In addition, links (14) may be somewhat bent laterally along their lengths.

Features such as these direct the overall artificial sphincter (10) to form a closed loop that can resiliently enlarge and contract between maximum and minimum closed loop sizes without mechanical interference therebetween. Magnets (36) in beads (12, 16) resiliently attract adjacent beads (12, 16) into contact with one another as shown in FIGS. 1, 3, and 5. However, this magnetic attraction between adjacent beads (12, 16) can be overcome, e.g., by sufficiently forceful radial enlargement of a patient's body tissue structure that passes through the interior (13) of the closed loop of beads (12, 16). For example, beads (12, 16) may be separated from one another in the annular direction by temporary radial enlargement of an esophagus (48) (see FIG. 7) (e.g., due to swallowing of a bolus of food). By way of further example, FIG. 4 shows an extreme upper limit of annular enlargement of artificial sphincter (10) to the maximum closed loop size. This enlargement limit is reached when each link (14) is pulled as far out of each bead (12) as enlarged stops (42) on the ends of links (14) will permit. Annular enlargement of artificial sphincter (10) is thus stopped by enlargement to this condition.

During annular enlargement, artificial sphincter (10) is resiliently urged to return to its fully, annularly contracted condition by the magnetic attraction between beads (12, 16). Annular contraction of artificial sphincter (10) is, however, ultimately limited by each bead (12, 16) coming into contact with adjacent beads (12, 16) in the string or loop. When each bead (12, 16) is in contact with adjacent beads (12, 16) as shown in FIGS. 1, 3, and 5, beads (12, 16) inhibit any further annular contraction of artificial sphincter (10). Artificial sphincter (10) is completely stable in this condition. Beyond this point, artificial sphincter (10) applies no additional pressure to the patient's body tissue structure that passes through the interior (13) of artificial sphincter (10). In some examples, this self-stopping or self-limiting contraction of artificial sphincter (10) may be beneficial for preserving the usefulness of tissue passing through artificial sphincter (10). For example, constant pressure may cause necrosis of the tissue. Thus, interior (13) of artificial sphincter (10) always remains at least as open as shown in FIG. 1, even if there were no tissue through the interior (13). Additional features that may be incorporated into artificial sphincter (10) are shown and described in U.S. Pat. Pub. No. 2014/0336696, entitled "Methods and Apparatus for Treating Body Tissue Sphincters and the Like," published on Nov. 13, 2014, issued as U.S. Pat. No. 10,398,440 on Sep. 3, 2019, as well as U.S. patent application Ser. No. 15/914,407, entitled "MRI Compatible Magnetic Sphincter Augmentation Device," filed Mar. 7, 2018, issued as U.S. Pat. No. 10,813,737 on Oct. 27, 2020, the disclosures of which are hereby incorporated by reference herein.

II. Exemplary Coupling Bead for Securing an Artificial Sphincter in a Closed Loop In order to secure left and right end segments (18, 20) of coupling bead (16) as shown in FIGS. 1-5, a catch clasp (50) has a left clasp portion (52) and a right clasp portion (54) respectively positioned on left and right end segments (18, 20). In the present example, left clasp portion (52) includes a left projection (56) and a corresponding left recess (58) opening in a radial direction, whereas right clasp portion (54) includes a right projection (60) and a corresponding right recess (62) opening in another, opposing radial direction. In this respect, right and left clasp portions (52, 54) respectively have like, albeit opposing, left and right U-shapes (64, 66) defined by projections (56, 60) and recesses (58, 62). Right projection (60) mates within left recess (58), while left projection (56) mates within right recess (62). In turn, left and right projections (56, 60) longitudinally overlap to interlock in the longitudinal direction. Friction and/or magnetic attraction may further radially secure left and right projections (56, 60) within right and left recesses (62, 58) although additional structures, such as those discussed below, may be used for additional securement in the longitudinal or radial direction.

During implantation of artificial sphincter (10), the surgeon directly manipulates left and right end segments (18, 20) relative to each other into a predetermined orientation. From the predetermined orientation, disconnected left clasp portion (52) and right clasp portion (54) longitudinally, radially, and rotatably align to simultaneously insert right projection (60) radially into left recess (58) and left projection (56) radially into right recess (62) for connection in the connected state. Beads (12, 16) and links (14) thereby define the closed loop for use.

While such direct manipulation may effectively position left and right end segments (18, 20) relative to each other into the predetermined orientation for connection of catch clasp (50) in some instances, such segments (18, 20) may be difficult to grasp and respectively orient. By way of example, the surgeon may have difficulty grasping left and right end segments (18, 20) by hand or with various surgical tools due a shape of the particular anatomy, available workspace around the anatomy, or the presence of patient fluids. Various coupling guides (72, 172, 272, 372, 472, 572, 672) configured to be grasped by the surgeon in order to aid alignment of left and right end segments (18, 20) to the predetermined orientation are described below in greater detail for more easily closing beads (12, 16) and links (14) in the closed loop. In addition to catch clasp (50), various alternative clasps (350, 450, 550) are further described below and may incorporate such coupling guides (72, 172, 272, 372, 472, 572, 672) for a variety of connections and predetermined orientations that may be tailored to the particular use in a given circumstance. Thereby, such coupling guides (72, 172, 272, 372, 472, 572, 672) and/or clasps (50, 350, 450, 550) improve manipulation of left and right end segments (18, 20) in some examples and, in turn, expedite surgery in order to improve patient outcomes. For continuity and consistency with examples described herein, like numbers indicate like features referenced below.

A. Grip Anchor Coupling Assembly

Figure 6:
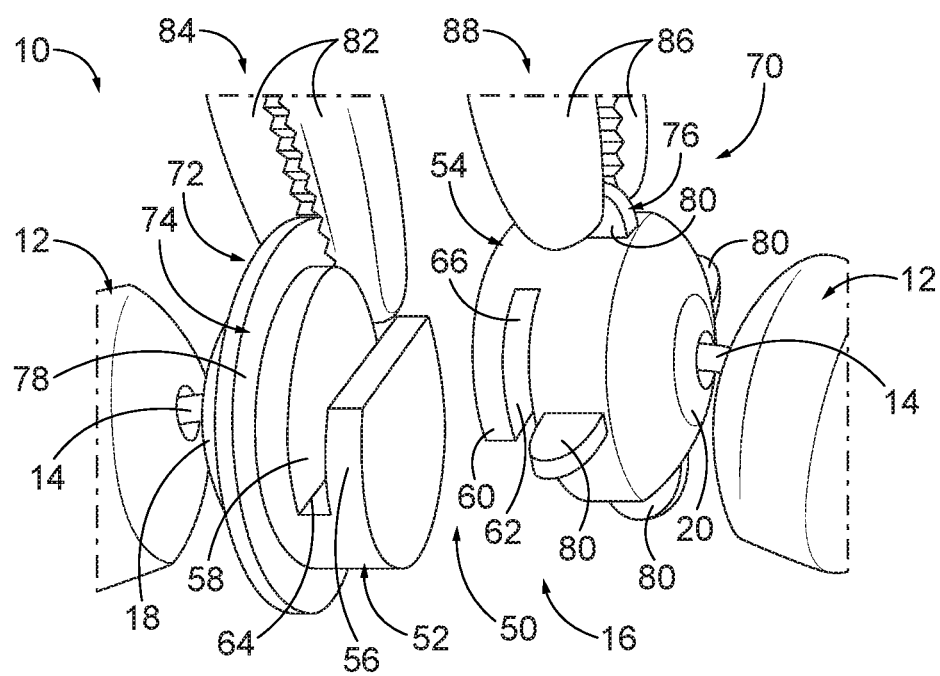
FIG. 6 depicts a perspective view of the artificial sphincter of FIG. 1 with a coupling bead and a grip anchor coupling guide in a disconnected state.
Figure 7:
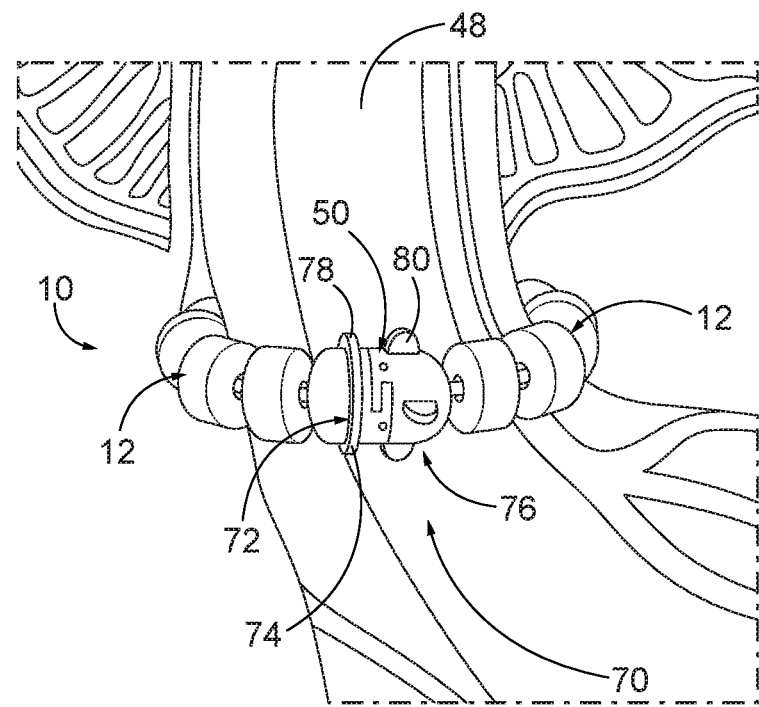
FIG. 7 depicts a perspective view of the grip anchor coupling bead of FIG. 6 in a connected state secured around a gastrointestinal tract.

FIGS. 6-7 show a grip anchor coupling assembly (70) including catch clasp (50) as well as a grip anchor coupling guide (72). As discussed above in greater detail, left and right clasp portions (52, 54) of catch clasp (50) extend toward each other from left and right end segments (18, 20) of coupling bead (16), respectively. Left clasp portion (52) has left projection (56) and left recess (58) defining left U-shape (64), whereas right clasp portion (54) has right projection (60) and right recess (62) defining right U-shape (66). Grip anchor coupling guide (72) similarly has a left guide portion (74) positioned on left end segment (18) and a right guide portion (76) positioned on right end segment (20). Left and right guide portions (74, 76) are configured to be manipulated relative to each other to thereby orient left U-shape (64) relative to right U-shape (66) to a predetermined orientation for left and right clasp portions (52, 54) and thereby connect in the connected state.

More particularly, in the present example shown in FIG. 6, left guide portion (74) includes an annular rigid projection (78) radially extending from left end segment (18), and right guide portion (76) includes a plurality of rigid tab projections (80) radially extending from right end segment (20). Annular rigid projection (78) surrounds left end segment (18) about a left central longitudinal axis through left end segment (18) as to be generally planar and perpendicular to the central longitudinal axis. The plurality of rigid tab projections (80) include four such rigid tab projections (80) equiangularly positioned about right end segment (20). Each rigid tab projection (80) is generally planar and parallel with a right central longitudinal axis through right end segment (20) such that rigid tab projections (80) are transverse to annular rigid projections (78) in the connected state. Thus, a pair of jaws (82) of one exemplary surgical tool (84) may be oriented transverse, such as 90 degrees, to a pair of jaws (86) of another exemplary surgical tool (88) to more easily manipulate and position left guide portion (74) relative to right guide portion (76) for the predetermined orientation of connection.

In use, the surgeon grasps annular rigid projection (78) of left guide portion (74) with jaws (82) of surgical tool (84) and further grasps at least one of rigid tab projections (80) of right guide portion (76) with jaws (86) of surgical tool (88). With respective sets of jaws (82, 86), the surgeon manipulates annular rigid projection (78) to be transverse to rigid tab projections (80) and orients left and right end segments (18, 20) toward each other to the predetermined orientation for left and right clasp portions (52, 54). From the predetermined orientation, the surgeon inserts left and right projections (56, 60) into right and left (62, 58) recesses to mate left clasp portion (52) to right clasp portion (54) from the disconnected state to the connected state for forming the closed loop of artificial sphincter (10) around the esophagus (48) as shown in FIG. 7.

B. Guide Collar Coupling Assembly

FIGS. 8A-8D show a guide collar coupling assembly (170) including catch clasp (50) as well as a collar coupling guide (172). As discussed above in greater detail, left and right clasp portions (52, 54) of catch clasp (50) extend toward each other from left and right end segments (18, 20) of coupling bead (16), respectively. Left clasp portion (52) has left projection (56) and left recess (58) defining left U-shape (64), whereas right clasp portion (54) has right projection (60) and right recess (62) defining right U-shape (66). Collar coupling guide (172) similarly has a left guide portion (174) positioned on left end segment (18) and a right guide portion (176) positioned on right end segment (20). Left and right guide portions (174, 176) are configured to be manipulated relative to each other to thereby orient left U-shape (64) relative to right U-shape (66) to a predetermined orientation for left and right clasp portions (52, 54) and thereby connect in the connected state.

Figure 8A:
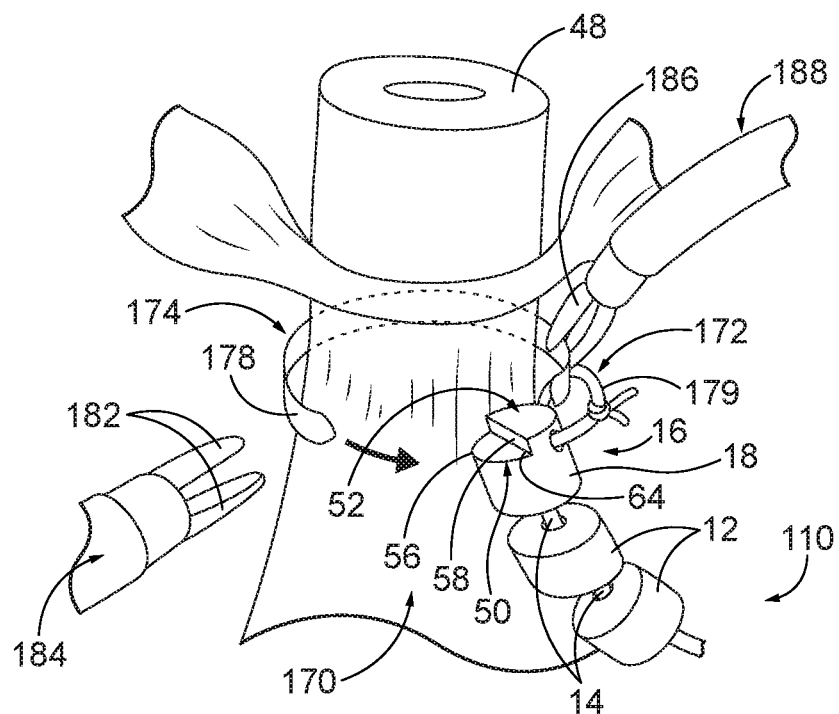
FIG. 8A depicts a perspective view of the coupling bead of FIG. 6 with a collar coupling guide being introduced around a gastrointestinal tract in a disconnected state.
Figure 8B:
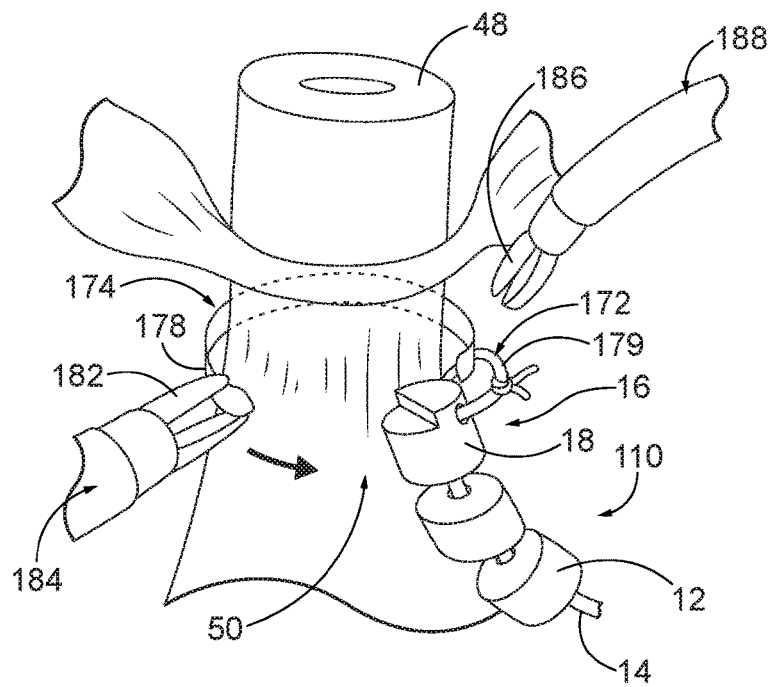
FIG. 8B depicts the perspective view of the collar coupling guide similar to FIG. 8A, but showing the collar coupling guide pulling a remainder of an artificial sphincter around a gastrointestinal tract.
Figure 8C:
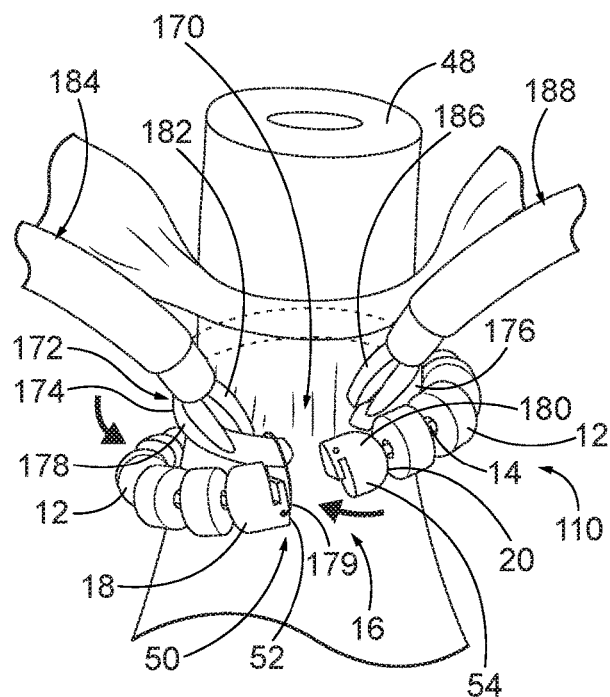
FIG. 8C depicts the perspective view of the collar coupling guide similar to FIG. 8B, but showing the collar coupling guide manipulated together toward the connected state.

More particularly, in the present example shown in FIG. 8B-8C, left guide portion (174) includes a collar (178) connected to left end segment (18) by a guide tie (179) such that left end segment (18) essentially hangs from collar (178) via guide tie (179). Collar (178) has a predetermined C-shape with lateral flexibility in its radial direction in order to be introduced around the esophagus (48) while pulling a remainder of an artificial sphincter (110) therebehind. Collar (178) may be grasped by a pair of jaws (182) of a surgical tool (184) while left end segment (18) hangs from guide tie (179). In contrast, right guide portion (176) has a grip surface (180) on right end segment (20) configured to be grasped by a pair of jaws (186) of another surgical tool (188). Thus, jaws (182) and jaws (184) respectively grasp an end portion of collar (178) and grip surface (180) on right end segment (20) to more easily manipulate and position left guide portion (174) relative to right guide portion (176) for the predetermined orientation of connection shown in FIG. 8D.

Figure 8D:
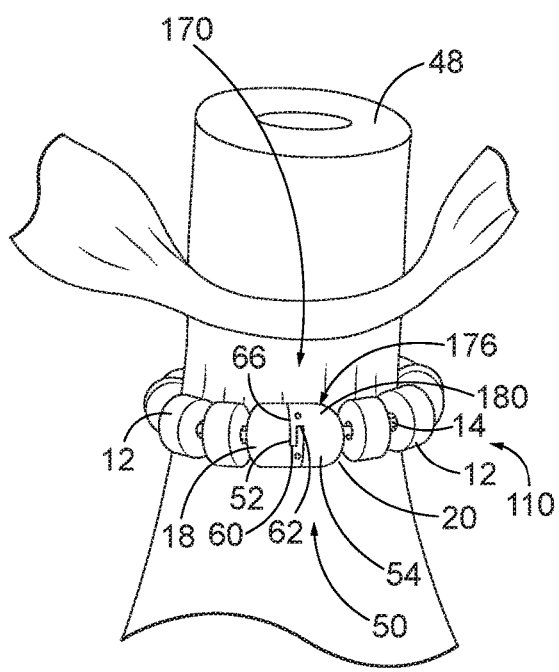
FIG. 8D depicts the perspective view of the collar coupling guide similar to FIG. 8C, but showing the coupling bead in the connected state.

In use, with respect to FIGS. 8A-8B, the surgeon successively grasps collar (178) and manipulates collar (178) around esophagus (48) the jaws (182, 186) such that the remainder of artificial sphincter (110) hangs from guide tie (179) The surgeon continues by orbiting collar (178) around esophagus (48) and, in turn, pulling the remainder of artificial sphincter (110) behind until artificial sphincter (110) is similarly positioned around esophagus (48) as shown in FIG. 8C. Jaws (182) grasps collar (178) while jaws (186) grasp grip surface (180) to respectively orient left and right end segments (18, 20) toward each other to the predetermined orientation for left and right clasp portions (52, 54). From the predetermined orientation, the surgeon inserts left and right projections (56, 60) into right and left (62, 58) recesses to mate left clasp portion (52) to right clasp portion (54) from the disconnected state to the connected state for forming the closed loop of artificial sphincter (110) around the esophagus (48) as shown in FIG. 8D. Once formed, the surgeon cuts guide tie (179) and removes guide tie (179) and collar 178) from the remainder of artificial sphincter (110) and from the patient altogether.

C. Pull-Tie Coupling Assembly

Figure 9A:
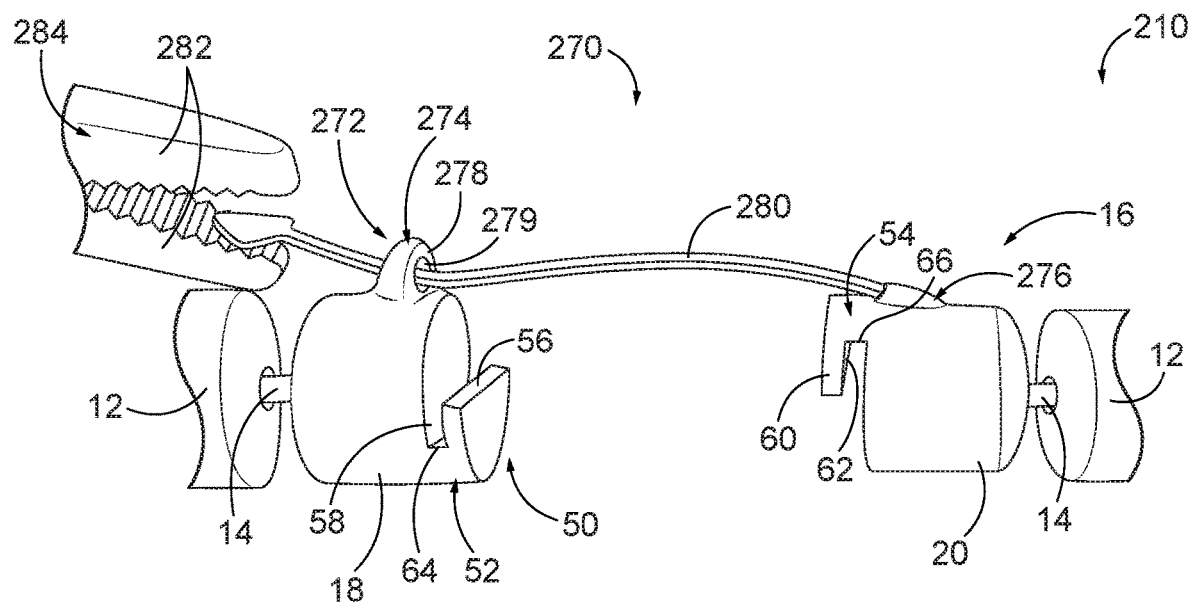
FIG. 9A depicts a perspective view of the coupling bead of FIG. 6 with a pull-tie coupling guide in a disconnected state.
Figure 9B:
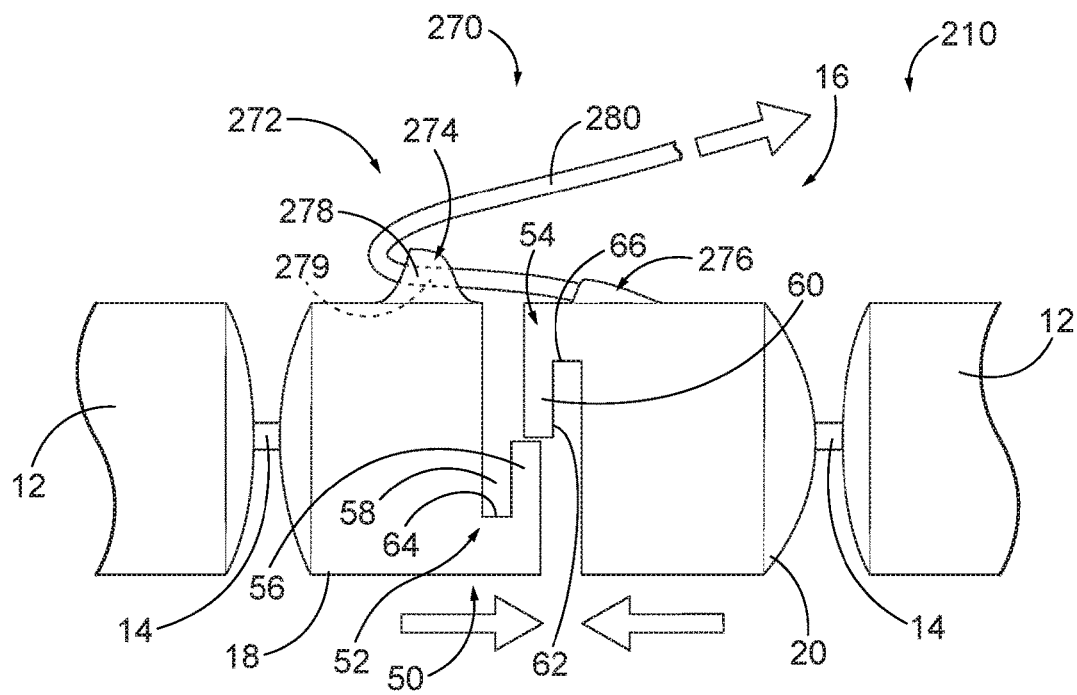
FIG. 9B, depicts the perspective view of the coupling bead and the pull-tie coupling guide similar to FIG. 9A, but showing the pull-tie coupling guide and the coupling bead being manipulated from the disconnected state toward a connected state.

FIGS. 9A-9B show a pull-tie coupling assembly (270) including catch clasp (50) as well as a pull-tie coupling guide (272). As discussed above in greater detail, left and right clasp portions (52, 54) of catch clasp (50) extend toward each other from left and right end segments (18, 20) of coupling bead (16), respectively. Left clasp portion (52)

has left projection (56) and left recess (58) defining left U-shape (64), whereas right clasp portion (54) has right projection (60) and right recess (62) defining right U-shape (66). Pull-tie coupling guide (272) similarly has a left guide portion (274) positioned on left end segment (18) and a right guide portion (276) positioned on right end segment (20). Left and right guide portions (274, 276) are configured to be manipulated relative to each other to thereby orient left U-shape (64) relative to right U-shape (66) to a predetermined orientation for left and right clasp portions (52, 54) and thereby connect in the connected state.

More particularly, in the present example shown in FIG. 9A, left guide portion (274) includes a ridge (278) radially extending from left end segment (18) that defines a through-hole (279) in the longitudinal direction, and right guide portion (276) includes a pull-tie (280) on right end segment (20) longitudinally extending therefrom. Pull-tie (280) is flexible and configured to be grasped by a pair of jaws (282) and inserted into through-hole (279). Thus, jaws (282) draw pull-tie (280) back through through-hole (279) in ridge (278) to more easily manipulate and position left guide portion (274) relative to right guide portion (276) for the predetermined orientation of connection.

In use, FIG. 9A shows the surgeon grasping an end portion of pull-tie (280) of right guide portion (276) with jaws (282) and inserting pull-tie (280) into through-hole (279). The surgeon releases and again grasps the end portion of pull-tie (280) and draws the end portion of pull-tie (280) further through through-hole (279) and back toward right end segment (20). Thereby, pull-tie (280) tightens and pulls left end segment (18) toward right end segment (20) to the predetermined orientation for left and right clasp portions (52, 54). From the predetermined orientation of FIG. 9B, the surgeon inserts left and right projections (56, 60) into right and left (62, 58) recesses to mate left clasp portion (52) to right clasp portion (54) from the disconnected state to the connected state for forming the closed loop of an artificial sphincter (210) around the esophagus (48) (see FIG. 8D).

D. Hitch Pin Coupling Assembly

Figure 10:
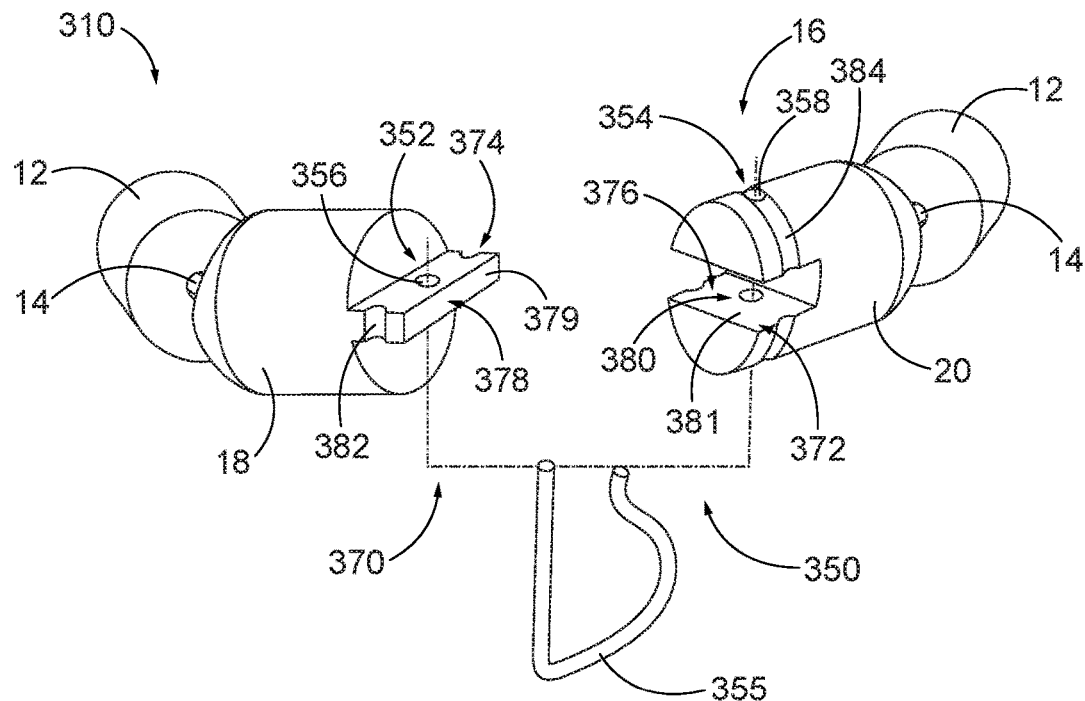
FIG. 10 depicts a perspective view the coupling bead of FIG. 6 with a hitch pin coupling guide in a disconnected state.
Figure 11:
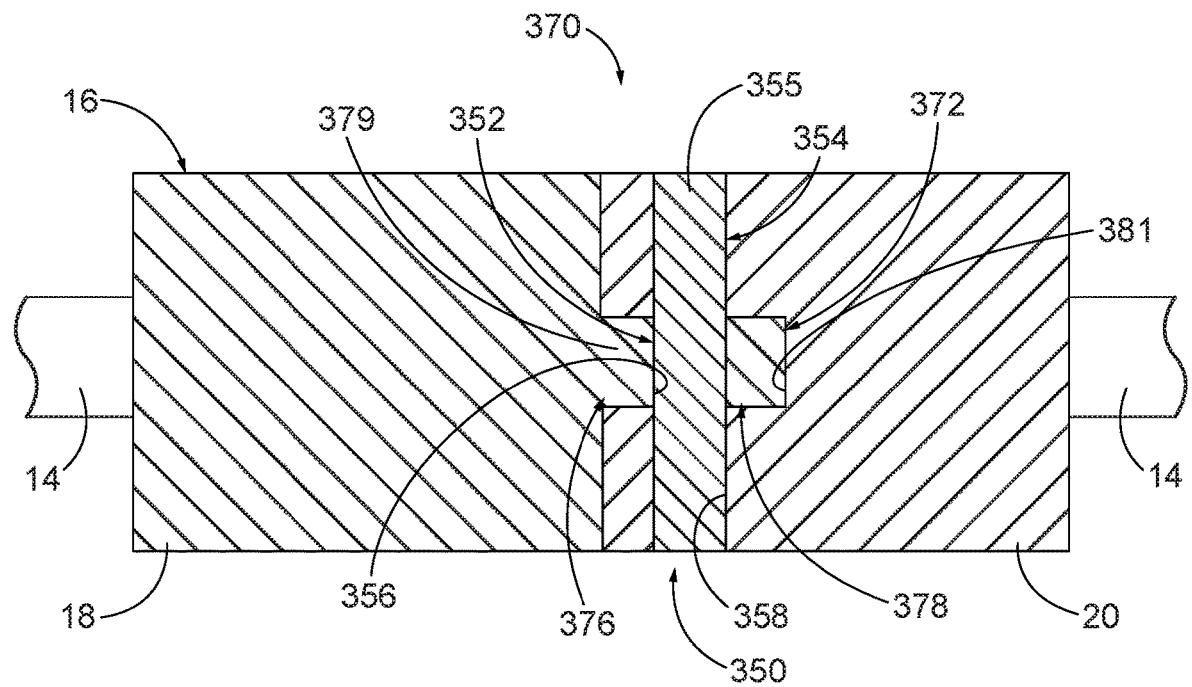
FIG. 11 depicts a cross-sectional view of the coupling bead and the hitch pin coupling guide of FIG. 10 taken along a centerline thereof in a connected state.

FIGS. 10-11 show a hitch pin coupling assembly (370) including a pin clasp (350) as well as a tongue-and-groove coupling guide (372). Pin clasp (350) has a left clasp portion (352) and a right clasp portion (354) respectively positioned on left and right end segments (18, 20) as well as a cotter pin (355). More particularly, left clasp portion (352) includes a left radial hole (356), right clasp portion (354) includes a right radial hole (358), and cotter pin (355) is configured to be simultaneously received within left and right radial holes (356, 358) to thereby secure left and right end segments (18, 20) when left and right end segments (18, 20) are in the predetermined orientation for left and right clasp portions (352, 354).

To this end, tongue-and-groove coupling guide (372) has a left guide portion (374) on left end segment (18) and a right guide portion (376) on a right end segment (20) collectively configured to guide left and right end segments (18, 20) with left and right clasp portions (352, 354) to the predetermined orientation. Left guide portion (374) of the present example includes a longitudinal extension (378) extending in a longitudinal direction from left end segment (18) and defining a tongue (379). Tongue (379) centrally extends along a central longitudinal axis of left end segment (18) and has a radial width equivalent to a radial diameter of left end segment (18). Right guide portion (376) of the present example includes a longitudinal slot (380) extending in the longitudinal direction through right end segment (20) and includes a groove (381). Like tongue (379), groove (381) centrally extends along a central longitudinal axis of right end segment (20) and has a radial width equivalent to a radial diameter of right end segment (20). Left radial hole (356) discussed above also extends radially through tongue (379) for alignment with right radial hole (358), which radially intersects through groove (381). Furthermore, in the present example, a left annular channel (382) extends around an outer radial surface of tongue (379) and a complementary right annular channel (384) extends around an outer radial surface of right end segment (20). Left and right annular channels (382, 384) longitudinally align to receive cotter pin (355) to reduce radial projection of cotter pin (355) relative to left and right end segments (18, 20) when in the connected state.

In use, the surgeon grasps left and right end segments (18, 20) and introduces tongue (379) into groove (381). Once introduced, the surgeon continues directing left and right end segments (18, 20) longitudinally together as tongue (379) and groove (381) provide radial guidance. Left and right end segments (18, 20) continue to longitudinally move toward each other until left end segment (18) contacts right end segment (20) and left and right annular channels (382, 384) as well as left and right radial holes (356, 358) longitudinally and radially align in the predetermined orientation for left and right clasp portions (352, 354). From the predetermined orientation, the surgeon then slides a portion of cotter pin (355) through left and right radial holes (356, 357), while another portion of cotter pin (255) slides through left and right annular channels (384). Left clasp portion (352) thereby mates with right clasp portion (354) from the disconnected state to the connected state for forming the closed loop of an artificial sphincter (310) around the esophagus (48) (see FIG. 7).

E. Outer Bayonet Coupling Assembly

Figure 12A:
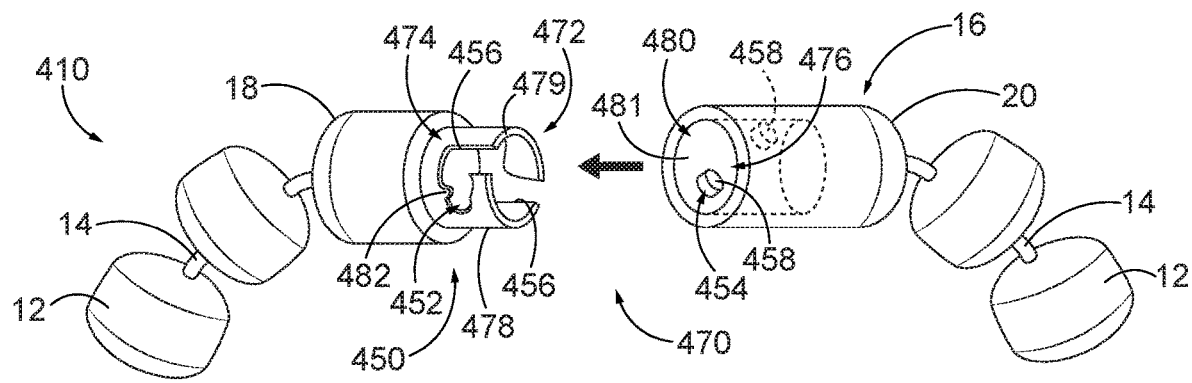
FIG. 12A depicts a perspective view of the coupling bead of FIG. 6 with a dowel coupling guide in a disconnected state.
Figure 12B:
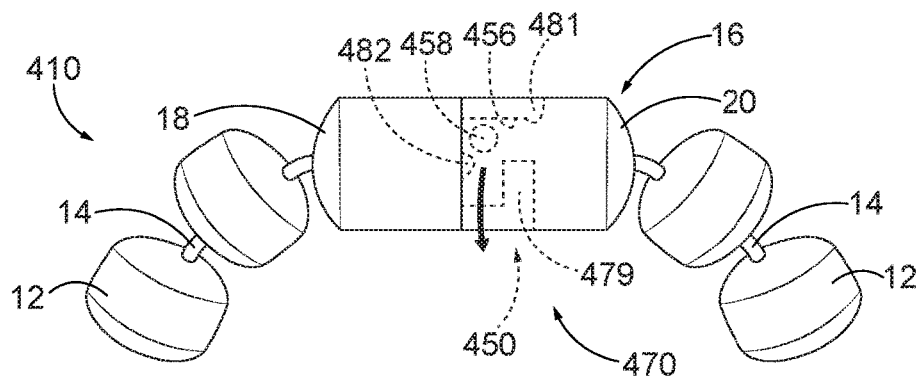
FIG. 12B depicts the perspective view of the coupling bead and the dowel coupling guide similar to FIG. 12A, but showing the dowel coupling guide and the coupling bead partially closed from the disconnected state toward the connected state.
Figure 12C:
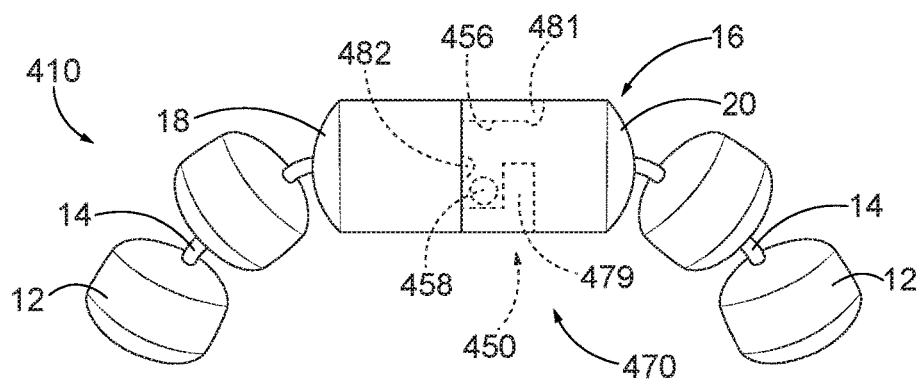
FIG. 12C depicts the perspective view of the coupling bead and the dowel coupling guide similar to FIG. 12B, but showing the dowel coupling guide and the coupling bead in the connected state.

FIGS. 12A-12C show an outer bayonet coupling assembly (470) including an outer bayonet clasp (450) as well as a dowel coupling guide (472). Outer bayonet clasp (450) has a left clasp portion (452) and a right clasp portion (454) respectively positioned on left and right end segments (18, 20). More particularly, left clasp portion (452) includes a pair of opposing bayonet slots (456), each having a longitudinal portion and a transverse portion, and right clasp portion (454) includes a pair of opposing and inwardly extending bayonet tabs (458). Bayonet slots (456) respectively receive bayonet tabs (458) in the transverse portions thereof to thereby secure left and right end segments (18, 20) when left and right end segments (18, 20) are in the predetermined orientation for left and right clasp portions (452, 454).

To this end, dowel coupling guide (472) has a left guide portion (474) on left end segment (18) and a right guide portion (476) on a right end segment (20) collectively configured to guide left and right end segments (18, 20) with left and right clasp portions (452, 454) to the predetermined orientation. Left guide portion (474) of the present example includes a longitudinal extension (478) extending in a longitudinal direction from left end segment (18) and defining a hollow dowel (479). Dowel (479) centrally extends along a central longitudinal axis of left end segment (18) and has a diameter less than a diameter of left end segment (18). Right guide portion (476) of the present example includes a longitudinal slot (480) extending in the longitudinal direction through right end segment (20) and includes a dowel hole (481). Like dowel (479), dowel hole (481) centrally extends along a central longitudinal axis of right end segment (20) and has a diameter smaller than a diameter of right end segment (20). Bayonet slots (456) discussed above also extend radially through dowel (479) for respectively receiving bayonet tabs (458), which radially and inwardly extend into dowel hole (481). Furthermore, in the present example, a resilient detent (482) extends from dowel (479) into the transverse portion of each respective bayonet slot (456). Resilient detents (482) are configured to resiliently secure bayonet tabs (458) in the transverse portions of bayonet slots (456) in order to maintain left and right end segments (18, 20) in the connected state.

In use, the surgeon grasps left and right end segments (18, 20) and introduces dowel (479) into dowel hole (481) as shown in FIGS. 12A-12B. Once introduced, the surgeon continues directing left and right end segments (18, 20) longitudinally together as dowel (479) and dowel hole (481) provide radial guidance. The longitudinal portions of bayonet slots (456) also receive bayonet tabs (458) when angularly aligned and longitudinally moved toward each other. Left and right end segments (18, 20) continue to longitudinally move toward each other until left end segment (18) contacts right end segment (20) and bayonet tabs (458) are introduced into the transverse portions of bayonet slots (456) as shown in FIG. 12B. With bayonet tabs (458) in the transverse portions of bayonet slots (456), left and right end segments (18, 20) with left and right clasp portions (452, 454) are in the predetermined orientation to be rotated relative to each other. Bayonet tabs (458) overcome resilient detents (482) to secure bayonet tabs (458) in the transverse portions of bayonet slots (456) to thereby mate with left and right clasp portions (452, 454) from the disconnected state to the connected state for forming the closed loop of an artificial sphincter (410) around the esophagus (48) (see FIG. 7).

F. Inner Bayonet Coupling Assembly

FIGS. 13A-16B show an inner bayonet coupling assembly (570) including an inner bayonet clasp (550) as well as a prong coupling guide (572). Inner bayonet clasp (550) has a left clasp portion (552) and a right clasp portion (554) respectively positioned on left and right end segments (18, 20). More particularly, left clasp portion (552) includes a pair of opposing bayonet slots (556), each having a longitudinal portion and a transverse portion, and right clasp portion (554) includes a pair of opposing and outwardly extending bayonet tabs (558). Bayonet slots (556) respectively receive bayonet tabs (558) in the transverse portions thereof to thereby secure left and right end segments (18, 20) when left and right end segments (18, 20) are in the predetermined orientation for left and right clasp portions (552, 554).

To this end, prong coupling guide (572) has a left guide portion (574) on left end segment (18) and a right guide portion (576) on a right end segment (20) collectively configured to guide left and right end segments (18, 20) with left and right clasp portions (552, 554) to the predetermined orientation. Left guide portion (574) of the present example includes a longitudinal slot 578 extending in a longitudinal direction through left end segment (18) and defining a receptacle hole (579). Receptacle hole (579) centrally extends along a central longitudinal axis of left end segment (18) and has a diameter smaller than a diameter of left end segment (18). Right guide portion (576) of the present example includes a longitudinal extension (580) extending in the longitudinal direction from right end segment (20) and define a prong (581). Like receptacle hole (579), prong (581) centrally extends along a central longitudinal axis from right end segment (20) and has a diameter less than a diameter of right end segment (20). Bayonet slots (556) discussed above also extend longitudinally and transversely through left end segment (18) in communication with receptacle hole (579) for respectively receiving bayonet tabs (558), which radially and outwardly extend from an end portion of prong (581).

Furthermore, in the present example, a magnetic detent (582) is configured to urge left end segment (18) with bayonet slots (556) to rotate relative to right end segment (20) with bayonet tabs (55) from the predetermined orientation in order to maintain left and right end segments (18, 20) in the connected state. Magnetic detent (582) of the present example includes a plurality of magnets (584) positioned on end faces of left and right end segments (18, 20) and face each other with opposing polarity to attract left and right end segments (18, 20) into connection. More particularly, four such magnets are equiangularly positioned about end faces of left and right end segments (18, 20). Magnetic detent (582) further includes a carrier (586) resiliently mounted on a biasing element (588), such as a wave spring, within right end segment (20) and longitudinally biased away from left end segment (18). Prong (581) with bayonet tabs (558) thereon extends from carrier (586) for use as discussed below.

Figure 13:
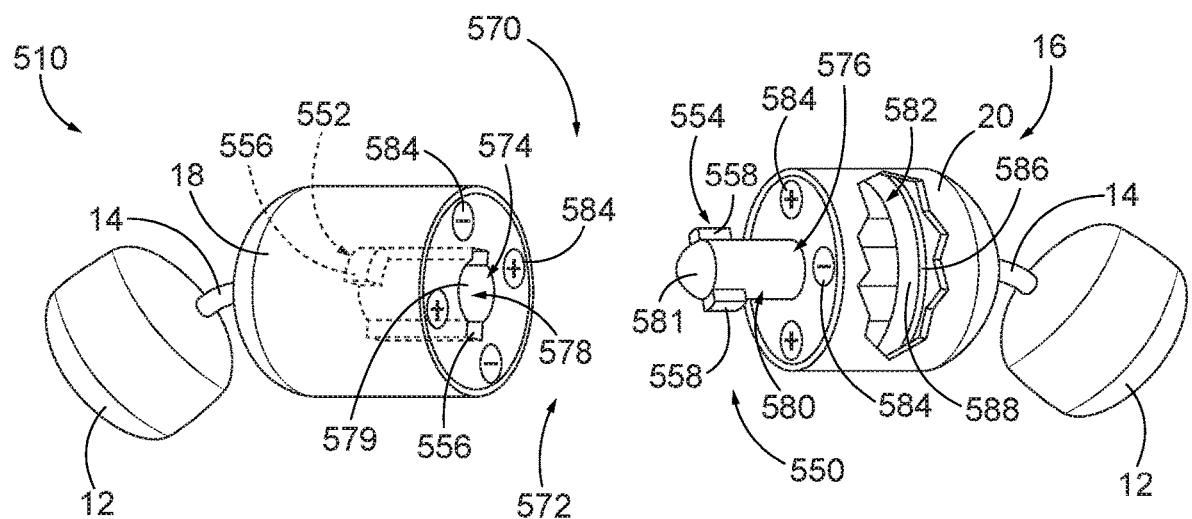
FIG. 13 depicts a perspective view of the coupling bead of FIG. 6 with a prong coupling guide in a disconnected state.
Figures 14, 15:
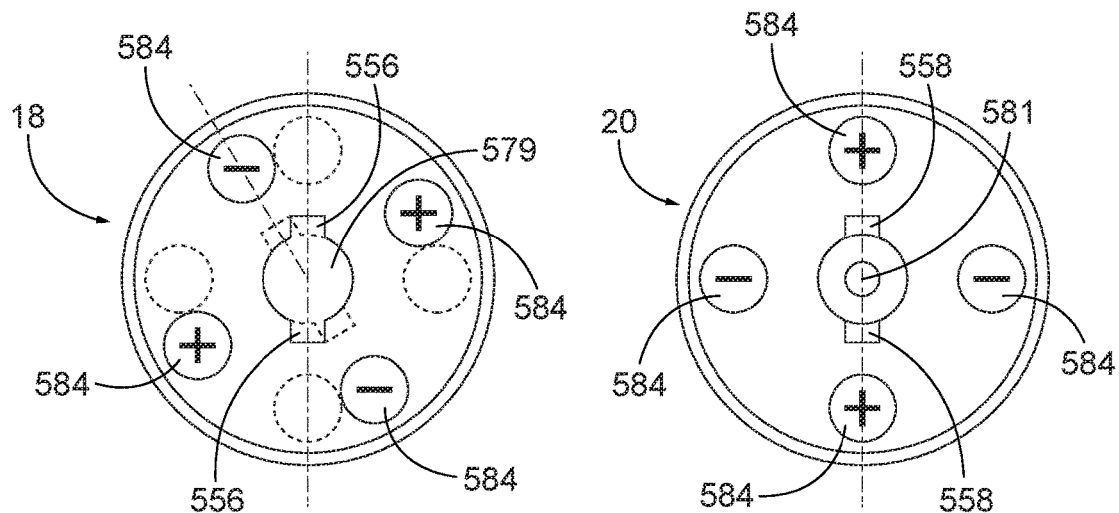
FIG. 14 depicts a right end side view of a left end segment of the coupling bead and a left guide portion of the prong coupling guide of FIG. 13.
FIG. 15 depicts a left end side view of a right end segment of the coupling bead and a right guide portion of the prong coupling guide of FIG. 13.
Figure 16A:
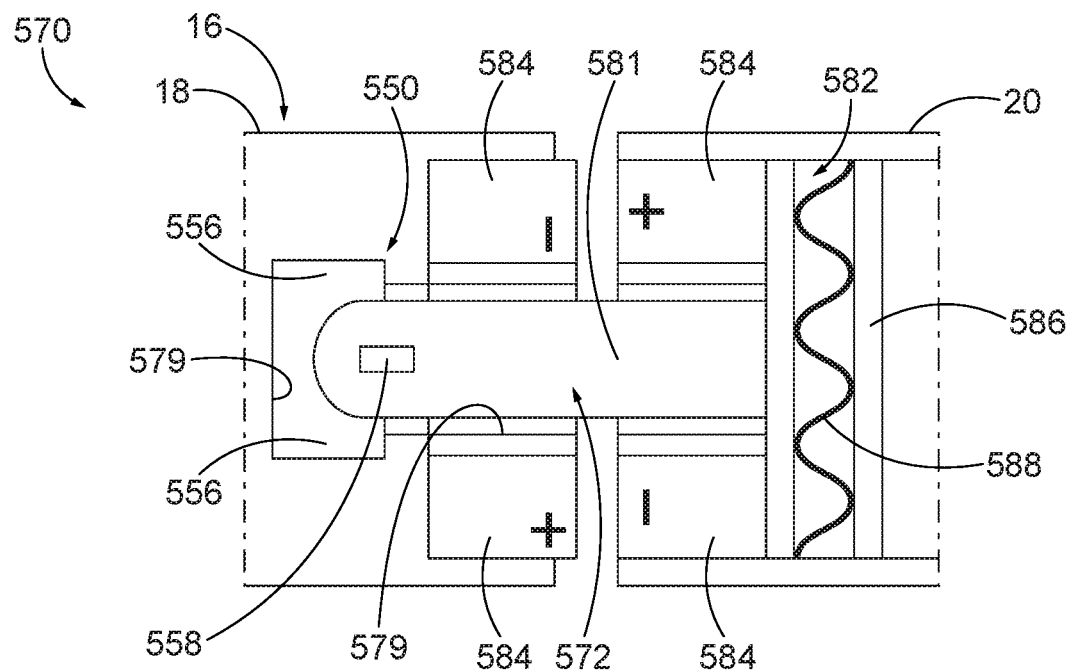
FIG. 16A depicts a sectional view of the coupling bead and the prong coupling guide of FIG. 13 partially closed from the disconnected state toward a connected state.
Figure 16B:
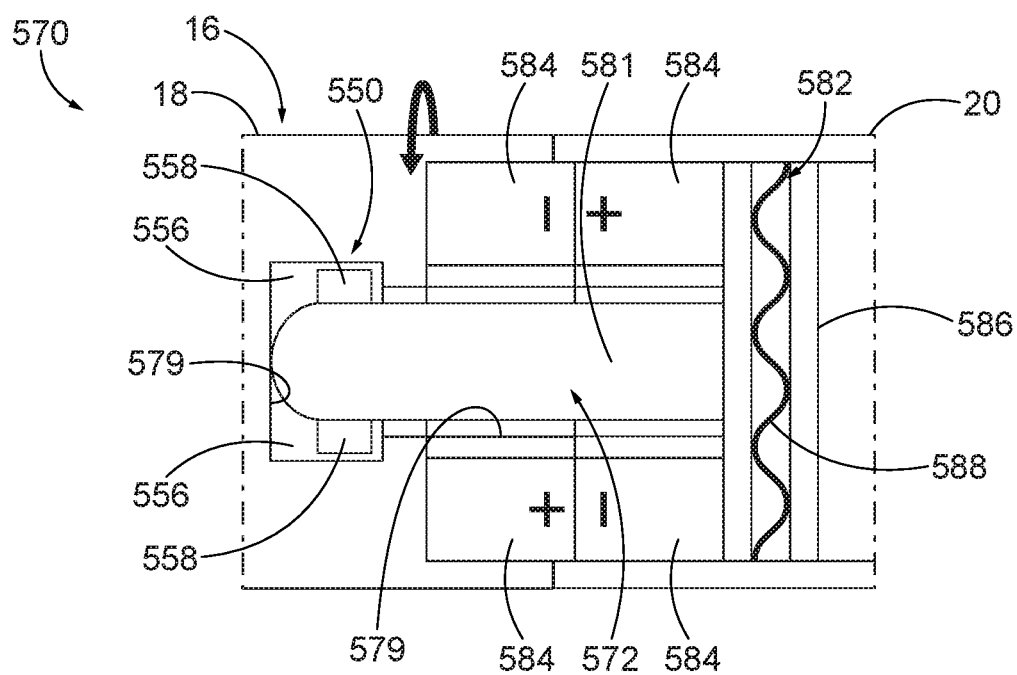
FIG. 16B depicts the perspective view of the coupling bead and prong coupling guide similar to FIG. 16A, but showing the prong coupling guide and the coupling bead in the connected state.

In use, the surgeon grasps left and right end segments (18, 20) and introduces prong (581) into receptacle hole (579) as shown in FIG. 13. Once introduced, the surgeon continues directing left and right end segments (18, 20) longitudinally together as prong (581) and receptacle hole (579) provide radial guidance. The longitudinal portions of bayonet slots (556) also receive bayonet tabs (558) when angularly aligned and longitudinally moved toward each other. Left and right end segments (18, 20) continue to longitudinally move toward each other until left end segment (18) contacts right end segment (20) and bayonet tabs (558) are introduced into the transverse portions of bayonet slots (556) as shown in FIGS. 14 and 16A. With bayonet tabs (558) in the transverse portions of bayonet slots (456), left and right end segments (18, 20) with left and right clasp portions (452, 454) are in the predetermined orientation to be rotated relative to each other. From the predetermined orientation, magnets (584) pull carrier (586) toward left end segment (18) thereby compressing biasing element (588). Bayonet tabs (558) are then rotated into bayonet slots (556) from the disconnected state to the connected state shown in FIGS. 15 and 16B for forming the closed loop of an artificial sphincter (510) around the esophagus (48) (see FIG. 7).

G. Clip Coupling Assembly

Figure 17A:
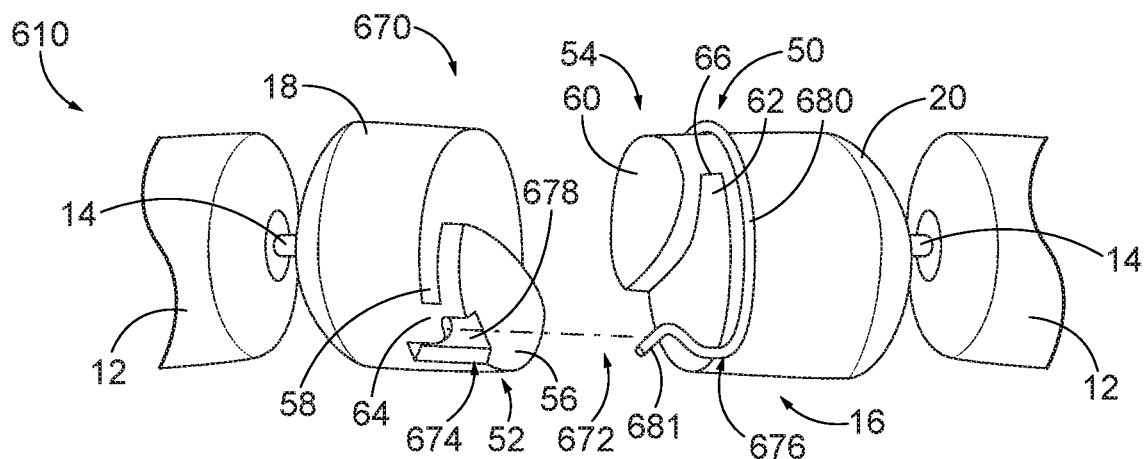
FIG. 17A depicts a perspective view of the coupling bead of FIG. 6 with a clip coupling guide in a disconnected state.
Figure 17B:
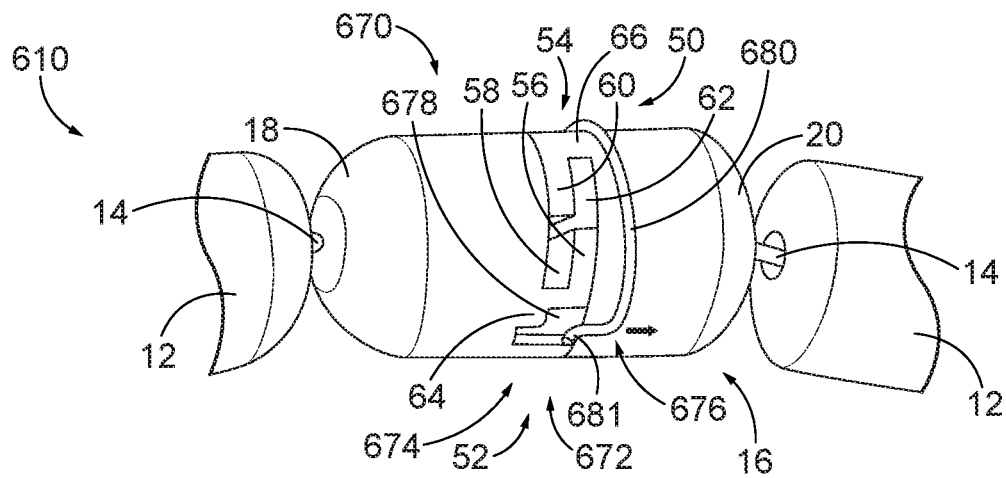
FIG. 17B depicts the perspective view of the coupling bead and the clip coupling guide similar to FIG. 17A, but showing the clip coupling guide and the coupling bead partially closed from the disconnected state toward the connected state.

FIGS. 17A-17B show a clip coupling assembly (670) including catch clasp (50) as well as a clip coupling guide (672). As discussed above in greater detail, left and right clasp portions (52, 54) of catch clasp (50) extend toward each other from left and right end segments (18, 20) of coupling bead (16), respectively. Left clasp portion (52) has left projection (56) and left recess (58) defining left U-shape (64), whereas right clasp portion (54) has right projection (60) and right recess (62) defining right U-shape (66). Clip coupling guide (672) similarly has a left guide portion (674) positioned on left end segment (18) and a right guide portion (676) positioned on right end segment (20). Left and right guide portions (674, 676) are configured to be manipulated relative to each other to thereby orient left U-shape (64) relative to right U-shape (66) to a predetermined orientation for left and right clasp portions (52, 54) and thereby connect in the connected state.

Figure 17C:
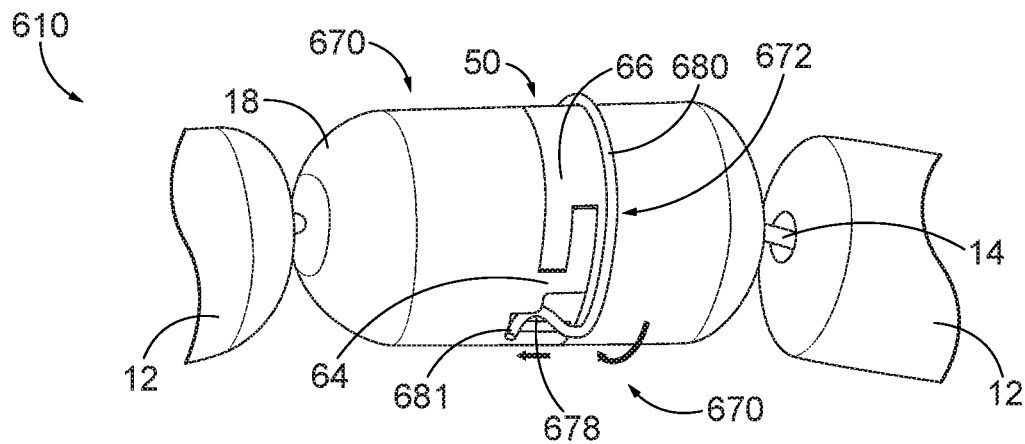
FIG. 17C depicts the perspective view of the coupling bead and the clip coupling guide similar to FIG. 17B, but showing the clip coupling guide and the coupling bead in the connected state.

More particularly, in the present example shown in FIG. 17A, left guide portion (674) includes a detent slot (678) radially and longitudinally extending into left end segment (18), and right guide portion (676) includes a ring clip (680) mounted on right end segment (20) around a portion of right end segment (20) and terminating at a terminal clip end (681) radially offset from right projection (60). In addition, left and right projections (56, 60) have chamfered corners to more easily abut left and right projections (56, 60) respectively against right and left end segments (18, 20). With respect to FIG. 17B, terminal clip end (681) is configured to be guided into a shallow portion of detent slot (678) as left and right end segments (18, 20) are brought longitudinally together. Terminal clip end (681) and detent slot (678) thereby guide left and right end segments (18, 20) to the predetermined orientation to more easily manipulate and position left and right end segments (18, 20) to the predetermined orientation. From the predetermined orientation, right end segment (20) and ring clip (68) are rotated together relative to left end segment (18) until terminal clip end (681) catches in a deeper portion of detent slot (678) for connection of left and right end segments (18, 20) in the connected state shown in FIG. 17C.

In use, FIG. 17A shows the surgeon directing left and right end segments (18, 20) longitudinally toward each other such that left and right projections (56, 60) respectively abut against right and left end segments (18, 20) as the shallow portion of detent slot (678) receives and guides terminal clip end (681) as shown in FIG. 17B. During such guidance, the shallow portion of detent slot (678) directs ring clip (680) and right end segment (20) attached thereto to the predetermined orientation. The surgeon then rotates left end segment (18) with detent slot (678) relative to right end segment (20) with ring clip (680) until terminal clip end (681) catches in the deeper portion of detent slot (678). In the present example, left and right end segments (18, 20) rotate about chamfered edges. From this position shown in FIG. 17C, left and right projections (56, 60) are received within right and left (62, 58) recesses to mate left clasp portion (52) to right clasp portion (54) from the disconnected state to the connected state for forming the closed loop of an artificial sphincter (610) around the esophagus (48) (see FIG. 8D).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An artificial sphincter, comprising: (a) a plurality of bodies including a first terminal body and a second terminal body successively arranged from the first terminal body to the second terminal body, wherein each of the plurality of bodies respectively includes a body magnet such that each of the plurality of bodies are magnetically attracted toward each other; (b) a plurality of links including a first terminal link and a second terminal link, wherein the plurality of links respectively resiliently extend and connect between the plurality of bodies and the first and second terminal links respectively extend from the first and second terminal bodies; (c) a coupling body having a first end segment and a second end segment respectively connected to the first and second terminal links; and (d) a coupling assembly, including: (i) a clasp having a first clasp portion and a second clasp portion respectively on the first and second end segments, wherein the first and second clasp portions are configured to connect together from a disconnected state to a connected state in a predetermined orientation such that the plurality of bodies and the coupling body define a closed loop in a contracted state, wherein the closed loop is configured resiliently expand from the contracted state toward an expanded state and is biased toward the contracted state, and (ii) a coupling guide having a first guide portion on the first end segment and a second guide portion on the second end segment, wherein the first and second guide portions are configured to be manipulated relative to each other to thereby orient the first clasp portion relative and the second clasp portion to the predetermined orientation for connection in the connected state.

Example 2

The artificial sphincter of Example 1, wherein the closed loop in the contracted state surrounds a predetermined minimum open interior configured to receive an anatomy of a patient, and wherein the closed loop in the expanded state surrounds an enlarged open interior having a larger area than the predetermined minimum open interior and is configured to accommodate the anatomy of the patient as the anatomy expands within the closed loop.

Example 3

The artificial sphincter of any one or more of Examples 1 through 2, wherein the first guide portion includes a first rigid projection fixed relative to the first clasp portion and radially extending outward from the first end segment, wherein the second guide portion includes a second rigid projection fixed relative to the second clasp portion and radially extending outward from the second end segment, and wherein each of the first and second rigid projections are configured to be grasped and manipulated to thereby position the first clasp portion relative to the second clasp portion in the predetermined orientation.

Example 4

The artificial sphincter of Example 3, wherein the first clasp portion includes a first U-shape, the second clasp portion includes a second U-shape, and the first and second U-shapes are configured to longitudinally interlock in the connected state.

Example 5

The artificial sphincter of any one or more of Examples 1 through 2, wherein the first guide portion includes a grip surface on the first end segment, wherein the second guide portion includes a collar and a guide tie connected between the collar and the second end segment, wherein the collar has a predetermined C-shape with lateral flexibility configured to be introduced around an anatomy of a patient, wherein the collar and the guide tie are configured to pull the second guide portion and remaining plurality of bodies around the anatomy and support the second end segment adjacent to first end segment for manipulation to the predetermined orientation.

Example 6

The artificial sphincter of Example 5, wherein the first clasp portion includes a first U-shape, the second clasp portion includes a second U-shape, and the first and second U-shapes are configured to longitudinally interlock in the connected state.

Example 7

The artificial sphincter of any one or more of Examples 1 through 2, wherein the first guide portion includes a pull tie extending from the first end segment, wherein the second guide portion includes a ridge extending from the second end segment and defining a hole therethrough, wherein the hole is configured to receive the pull tie introduced therethrough and thereby position the first clasp portion relative to the second clasp portion in the predetermined orientation.

Example 8

The artificial sphincter of Example 7, wherein the first clasp portion includes a first U-shape, the second clasp portion includes a second U-shape, and the first and second U-shapes are configured to longitudinally interlock in the connected state.

Example 9

The artificial sphincter of any one or more of Examples 1 through 2, wherein the first guide portion includes a detent slot in the first end segment, wherein the second guide portion includes a resilient clip attached to the second end segment, and wherein the detent slot is configured to receive the resilient clip to thereby position the first clasp portion relative to the second clasp portion in the predetermined orientation.

Example 10

The artificial sphincter of Example 9, wherein the first clasp portion includes a first U-shape, the second clasp portion includes a second U-shape, and the first and second U-shapes are configured to longitudinally interlock in the connected state.

Example 11

The artificial sphincter of any one or more of Examples 1 through 2, wherein the first guide portion includes a longitudinal extension extending from the first end segment, wherein the second guide portion includes a longitudinal slot within the second end segment, and wherein the longitudinal slot receives the longitudinal extension to thereby position the first clasp portion relative to the second clasp portion in the predetermined orientation.

Example 12

The artificial sphincter of Example 11, wherein the first clasp portion includes a first radial hole through the longitudinal extension, wherein the second clasp portion includes a second radial hole through the second end segment intersecting with the longitudinal slot, and wherein the coupling assembly further includes a pin configured to be received through each of the first and second radial holes to interlock the pin to each of the first and second end segments in the connected state.

Example 13

The artificial sphincter of Example 11, wherein the first clasp portion includes a radial bayonet slot extending through longitudinal extension, wherein the second clasp portion includes a radial tab extending radially inward into the longitudinal slot, and wherein the radial bayonet slot receives the radial tab to longitudinally interlock in the connected state.

Example 14

The artificial sphincter of any one or more of Example 13, wherein the first guide portion includes a first detent magnet attached to the first end segment, wherein the second guide portion includes a second detent magnet attached to the second end segment, and wherein the first and second detent magnets cooperatively urge the longitudinal extension into the longitudinal slot to direct the radial tab further along the radial bayonet slot toward the connected state.

Example 15

The artificial sphincter of Example 11, wherein the first clasp portion includes a radial tab extending radially outward from the longitudinal extension, wherein the second clasp portion includes a radial bayonet slot in communication with the longitudinal slot, and wherein the radial bayonet slot receives the radial tab to longitudinally interlock in the connected state.

Example 16

An artificial sphincter, comprising: (a) a plurality of bodies including a first terminal body and a second terminal body successively arranged from the first terminal body to the second terminal body, wherein each of the plurality of bodies respectively includes a body magnet such that each of the plurality of bodies are magnetically attracted toward each other; (b) a plurality of links including a first terminal link and a second terminal link, wherein the plurality of links respectively extend and connect between the plurality of bodies and the first and second terminal links respectively extend from the first and second terminal bodies; (c) a coupling body having a first end segment and a second end segment respectively connected to the first and second terminal links; and (d) a coupling assembly, including a clasp having a radial tab and a radial bayonet slot respectively on the first and second end segments, wherein the radial bayonet slot is configured to receive the radial tab to connect the clasp together from a disconnected state to a connected state in a predetermined orientation such that the plurality of bodies and the coupling body define a closed loop in a contracted state, wherein the closed loop is configured resiliently expand from the contracted state toward an expanded state and is biased toward the contracted state.

Example 17

The artificial sphincter of Example 16, wherein the coupling assembly further includes a coupling guide having a first guide portion on the first end segment and a second guide portion on the second end segment, wherein the first and second guide portions are configured to be manipulated relative to each other to thereby orient the radial tab relative to the radial bayonet slot to the connected state.

Example 18

The artificial sphincter of Example 17, wherein the first guide portion includes a first alignment magnet attached to the first end segment, wherein the second guide portion includes a second alignment magnet attached to the second end segment, and wherein the first and second alignment magnets cooperatively urge the first end segment relative to the second end segment to thereby interlock the radial tab in the radial bayonet slot in the connected state.

Example 19

The artificial sphincter of Example 16, wherein the closed loop in the contracted state surrounds a predetermined minimum open interior configured to receive an anatomy of a patient, and wherein the closed loop in the expanded state surrounds an enlarged open interior having a larger area than the predetermined minimum open interior and is configured to accommodate the anatomy of the patient as the anatomy expands within the closed loop.

Example 20

A method of closing an artificial sphincter to form a closed loop, wherein the artificial sphincter includes (a) a plurality of bodies including a first terminal body and a second terminal body successively arranged from the first terminal body to the second terminal body, wherein each of the plurality of bodies respectively includes a body magnet such that each of the plurality of bodies are magnetically attracted toward each other; (b) a plurality of links including a first terminal link and a second terminal link, wherein the plurality of links respectively resiliently extend and connect between the plurality of bodies and the first and second terminal links respectively extend from the first and second terminal bodies; (c) a coupling body having a first end segment and a second end segment respectively connected to the first and second terminal links; and (d) a coupling assembly, including: (i) a clasp having a first clasp portion and a second clasp portion respectively on the first and second end segments, wherein the first and second clasp portions are configured to connect together from a disconnected state to a connected state in a predetermined orientation such that the plurality of bodies and the coupling body define a closed loop in a contracted state, wherein the closed loop is configured resiliently expand from the contracted state toward an expanded state and is biased toward the contracted state, and (ii) a coupling guide having a first guide portion on the first end segment and a second guide portion on the second end segment, the method comprising: (a) manipulating the first guide portion relative to the second guide portion to thereby orient the first clasp portion relative to the second clasp portion to the predetermined orientation; and (b) connecting the first clasp portion to the second clasp portion in the connected state from the predetermined orientation to form the closed loop around an anatomy of a patient.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An artificial sphincter, comprising:
   (a) a plurality of bodies including a first terminal body and a second terminal body successively arranged from the first terminal body to the second terminal body, wherein each of the plurality of bodies respectively includes a body magnet such that each of the plurality of bodies are magnetically attracted toward each other;
   (b) a plurality of links including a first terminal link and a second terminal link, wherein the plurality of links respectively resiliently extend and connect between the plurality of bodies and the first and second terminal links respectively extend from the first and second terminal bodies;
   (c) a coupling body having a first end segment and a second end segment respectively connected to the first and second terminal links wherein the coupling body defines a central longitudinal axis; and
   (d) a coupling assembly, including:
      (i) a clasp having a first clasp portion and a second clasp portion respectively on the first and second end segments, wherein the first and second clasp portions are configured to connect together from a disconnected state to a connected state in a predetermined orientation such that the plurality of bodies and the coupling body define a closed loop in a contracted state, wherein the closed loop is configured to resiliently expand from the contracted state toward an expanded state and is biased toward the contracted state, and
      (ii) a coupling guide having a first guide portion on the first end segment and a second guide portion on the second end segment, wherein one of the first and second guide portions is configured to be translated along the central longitudinal axis toward the other of the first and second guide portions while in an unlocked configuration and is configured to be subsequently rotated about the central longitudinal axis into locking engagement with the other of the first and second guide portions at the predetermined orientation.

2. The artificial sphincter of claim 1, wherein the closed loop in the contracted state surrounds a predetermined minimum open interior configured to receive an anatomy of a patient, and wherein the closed loop in the expanded state surrounds an enlarged open interior having a larger area than the predetermined minimum open interior and is configured to accommodate the anatomy of the patient as the anatomy expands within the closed loop.

3. The artificial sphincter of claim 1, wherein the first clasp portion includes a first U-shape, the second clasp portion includes a second U-shape, and the first and second U-shapes are configured to longitudinally interlock in the connected state.

4. The artificial sphincter of claim 1, wherein the first guide portion includes a detent slot in the first end segment, wherein the second guide portion includes a resilient clip attached to the second end segment, and wherein the detent slot is configured to receive the resilient clip to thereby position the first clasp portion relative to the second clasp portion in the predetermined orientation.

5. The artificial sphincter of claim 4, wherein the first clasp portion includes a first U-shape, the second clasp portion includes a second U-shape, and the first and second U-shapes are configured to longitudinally interlock in the connected state.

6. The artificial sphincter of claim 1, wherein the first guide portion includes a longitudinal extension extending from the first end segment, wherein the second guide portion includes a longitudinal slot within the second end segment, and wherein the longitudinal slot receives the longitudinal extension to thereby position the first clasp portion relative to the second clasp portion in the predetermined orientation.

7. The artificial sphincter of claim 6, wherein the first clasp portion includes a radial bayonet slot extending through the longitudinal extension, wherein the second clasp portion includes a radial tab extending radially inward into the longitudinal slot, and wherein the radial bayonet slot receives the radial tab to longitudinally interlock in the connected state.

8. The artificial sphincter of claim 7, wherein the first guide portion includes a first detent magnet attached to the first end segment, wherein the second guide portion includes a second detent magnet attached to the second end segment, and wherein the first and second detent magnets cooperatively urge the longitudinal extension into the longitudinal slot to direct the radial tab further along the radial bayonet slot toward the connected state.

9. The artificial sphincter of claim 8, wherein the second clasp portion includes a biasing element configured to be biased due to a magnetic attraction between the first and second detent magnets.

10. The artificial sphincter of claim 6, wherein the first clasp portion includes a radial tab extending radially outward from the longitudinal extension, wherein the second clasp portion includes a radial bayonet slot in communication with the longitudinal slot, and wherein the radial bayonet slot receives the radial tab to longitudinally interlock in the connected state.

11. The artificial sphincter of claim 6, wherein the longitudinal extension extends from the first end segment along the central longitudinal axis.

12. A method of closing an artificial sphincter to form a closed loop, wherein the artificial sphincter includes (a) a plurality of bodies including a first terminal body and a second terminal body successively arranged from the first terminal body to the second terminal body, wherein each of the plurality of bodies respectively includes a body magnet such that each of the plurality of bodies are magnetically attracted toward each other; (b) a plurality of links including a first terminal link and a second terminal link, wherein the plurality of links respectively resiliently extend and connect between the plurality of bodies and the first and second terminal links respectively extend from the first and second terminal bodies; (c) a coupling body having a first end segment and a second end segment respectively connected to the first and second terminal links; and (d) a coupling assembly, including: (i) a clasp having a first clasp portion and a second clasp portion respectively on the first and second end segments, wherein the first and second clasp portions are configured to connect together along a central longitudinal axis such that the plurality of bodies and the coupling body define a closed loop in a contracted state, wherein the closed loop is configured to resiliently expand from the contracted state toward an expanded state and is biased toward the contracted state, and (ii) a coupling guide having a first guide portion on the first end segment and a second guide portion on the second end segment, the method comprising:

(a) translating the first guide portion relative to the second guide portion along the central longitudinal axis so that the first clasp portion contacts the second clasp portion in an unlocked configuration; and (b) subsequently rotating the first guide portion relative to the second guide portion in a first direction about the central longitudinal axis from the unlocked configuration to a predetermined orientation in a locked configuration to connect the first clasp portion to the second clasp portion in the predetermined orientation to form the closed loop around an anatomy of a patient.

13. The method of claim 12, further comprising rotating the first guide portion relative to the second guide portion in a second direction that is opposite the first direction along a central longitudinal axis from the locked configuration to the unlocked configuration to release the first clasp portion from the second clasp portion.

14. An artificial sphincter, comprising:

(a) a plurality of bodies including a first terminal body and a second terminal body successively arranged from the first terminal body to the second terminal body, wherein each of the plurality of bodies respectively includes a body magnet such that each of the plurality of bodies are magnetically attracted toward each other;

(b) a plurality of links including a first terminal link and a second terminal link, wherein the plurality of links respectively resiliently extend and connect between the plurality of bodies and the first and second terminal links respectively extend from the first and second terminal bodies;

(c) a coupling body having a first end segment and a second end segment respectively connected to the first and second terminal links; and (d) a coupling assembly comprising:

(i) a clasp including a first clasp portion and a second clasp portion respectively on the first and second end segments, wherein the first and second clasp portions are configured to connect together from a disconnected state to a connected state in a predetermined orientation such that the plurality of bodies and the coupling body define a closed loop in a contracted state, wherein the closed loop is configured to resiliently expand from the contracted state toward an expanded state and is biased toward the contracted state, and (ii) a coupling guide comprising:

(A) a first rigid projection disposed on an outer periphery of the first end segment, and (B) a second rigid projection disposed on an outer periphery of the second end segment, wherein the first and second rigid projections are configured to be manipulated by a user relative to each other to thereby orient the first clasp portion and the second clasp portion to the predetermined orientation in the connected state, wherein the first and second rigid projections are spaced apart a distance in the predetermined orientation in the connected state.

15. The artificial sphincter of claim 14, wherein at least one of the first and second rigid projections extends outwardly from the central longitudinal axis.

16. The artificial sphincter of claim 14, wherein the first rigid projection is fixed relative to the first clasp portion and extends radially outwardly from the first end segment, wherein the second rigid projection is fixed relative to the second clasp portion and extends radially outwardly from the second end segment, and wherein each of the first and second rigid projections is configured to be grasped and manipulated to thereby position the first clasp portion relative to the second clasp portion in the predetermined orientation.

17. The artificial sphincter of claim 14, wherein one of the first and second rigid projections includes an annular rigid projection.

18. The artificial sphincter of claim 14, wherein the first clasp portion includes a first U-shape, the second clasp portion includes a second U-shape, and the first and second U-shapes are configured to longitudinally interlock in the connected state.

19. The artificial sphincter of claim 14, further comprising a third rigid projection disposed on the outer periphery of the second end segment.

20. The artificial sphincter of claim 19, further comprising a fourth rigid projection disposed on the outer periphery of the second end segment, wherein the second, third, and fourth rigid projections are equiangularly spaced along the outer periphery of the second end segment.

* * * * *